US012586183B2

(12) United States Patent
Cochrane

(10) Patent No.: US 12,586,183 B2
(45) Date of Patent: Mar. 24, 2026

(54) METHOD FOR DIAGNOSING LATENT TUBERCULOSIS INFECTION

(71) Applicant: Oxford Immunotec Limited, Oxford (GB)

(72) Inventor: Daniel Cochrane, Oxford (GB)

(73) Assignee: Oxford Immunotec Limited, Oxford (GB)

( * ) Notice: Subject to any disclaimer, the term of this patent is extended or adjusted under 35 U.S.C. 154(b) by 504 days.

(21) Appl. No.: 18/041,963

(22) PCT Filed: Aug. 23, 2021

(86) PCT No.: PCT/GB2021/052180
§ 371 (c)(1),
(2) Date: Feb. 16, 2023

(87) PCT Pub. No.: WO2022/043669
PCT Pub. Date: Mar. 3, 2022

(65) Prior Publication Data
US 2023/0326015 A1 Oct. 12, 2023

(30) Foreign Application Priority Data

Aug. 24, 2020 (EP) .................................... 20192344

(51) Int. Cl.
*G06T 7/00* (2017.01)
*G06T 3/60* (2006.01)
(Continued)

(52) U.S. Cl.
CPC .............. *G06T 7/0012* (2013.01); *G06T 3/60* (2013.01); *G16B 20/00* (2019.02); *G16H 50/20* (2018.01);
(Continued)

(58) Field of Classification Search
None
See application file for complete search history.

(56) References Cited

U.S. PATENT DOCUMENTS

2016/0274104 A1 9/2016 Aminoff et al.
2021/0042916 A1* 2/2021 Zhang .................... G16H 50/70

FOREIGN PATENT DOCUMENTS

CN 111091127 A 5/2020

OTHER PUBLICATIONS

Abuhassan, et al.: "Automatic Diagnosis of Tuberculosis Disease Based on Plasmonic ELISA and Color-based Image Classification," 2017 39th Annual International Conference of the IEEE Engineering in Medicine and Biology Society (EMBC), IEEE, Jul. 11, 2017, pp. 4512-4515.

(Continued)

*Primary Examiner* — Lennin R Rodriguezgonzalez
(74) *Attorney, Agent, or Firm* — Norton Rose Fulbright US LLP

(57) ABSTRACT

The disclosure concerns a method of obtaining information about the disease status of an individual by processing input data using a trained machine learning algorithm model to generate an output representing the information. The disclosure also concerns a related computer program, data processing apparatus, and system, as well as a method for training a machine learning algorithm model to generate information about the disease status of an individual. The information may, for example, relate to the presence, absence or type of *M. tuberculosis* complex infection in the individual.

11 Claims, 20 Drawing Sheets

(51) Int. Cl.
    *G16B 20/00*       (2019.01)
    *G16H 50/20*      (2018.01)

(52) U.S. Cl.
    CPC .............. *G06T 2207/20081* (2013.01); *G06T 2207/20084* (2013.01); *G06T 2207/30024* (2013.01); *G06T 2207/30072* (2013.01)

(56) References Cited

OTHER PUBLICATIONS

T-SPOT. COVID. Package Insert. For in vitro Diagnostic Use of COV.435/300, COV.435/200, Oxford Immunotech, (2021), pp. 1-21; XP055856925, Retrieved from the Internet: URL:https://web.archive.org/web/20210421213435if_/https://www.tspotcovid.com/wp-content/uploads/sites/5/2021/03/PI-T-SPOT.COVID-IVD-UK-v3.pdf [retrieved on Nov. 2, 2021].

Janssens, et al.: "Quantitative scoring of an interferon-y assay for differentiating active from latent tuberculosis," European Respiratory Journal, 30(4), (2007), pp. 722-728.

Luo, et al.: "Combination of mean spot sizes of ESAT-6 spot-forming cells and modified tuberculosis-specific antigen/ phytohemagglutinin ratio of T-SPOT.TB assay in distinguishing between active tuberculosis and latent tuberculosis Infection," Journal of infection, 81(1), (2020), pp. 81-89.

Shabut, et al.: "An intelligent mobile-enabled expert system for tuberculosis disease diagnosis in real time," Expert Systems With Applications, 114, (2018), pp. 65-77.

Tania, et al.: "Assay Type Detection Using Advanced Machine Learning Algorithms," 2019 13th International Conference on Software, Knowledge, Information Management and Applications (SKIMA), IEEE, Aug. 26, 2019, pp. 1-8.

Wang, et al.: "Using the TBAg/PHA ratio in the T-SPOT.TB assay to distinguish TB disease from LTBI in an endemic area", Int. J. Tuberc. Lung Dis. 20(4), (2016), pp. 487-493.

Wang, et al.: "Combination of Xpert MTB/RIF and TBAg/PHA Ratio for Prompt Diagnosis of Active Tuberculosis: A Two-Center Prospective Cohort Study," frontiers in Medicine 7, (2020), Article 119, pp. 1-10.

Wyllie, et al.: "SARS-CoV-2 responsive T cell numbers and anti-Spike IgG levels are both associated with protection from COVID-19: A prospective cohort study in keyworkers", medRxiv, May 2, 2021, pp. 1-33.

International Search Report issued in PCT/GB2021/052180 on Oct. 11, 2021.

* cited by examiner

Original images

Nil    Panel A    Panel B    Positive

Composite image

Augmented image

Rotated image    Altered brightness image    Rotated and altered brightness image

A)

B)

A)

B)

B)

A)

A)

B)

A)

simdata sim data

ROC curve: ROC of simdata sim data

B)

simdata iq data

ROC curve: ROC of simdata iq data

Original Images

Original and rotated images

Original and altered brightness images

Original and all augmentation images combo ROC

A

B

A)

B)

METHOD FOR DIAGNOSING LATENT TUBERCULOSIS INFECTION

CROSS-REFERENCE TO RELATED APPLICATIONS

This application is a national phase application under 35 U.S.C. § 371 that claims priority to International Application No. PCT/GB2021/052180 filed Aug. 23, 2021, which claims priority to European Patent Application No. 20192344.8 filed Aug. 24, 2020, all of which are incorporated herein by reference in their entirety.

FIELD OF THE DISCLOSURE

The disclosure concerns a method of obtaining information about the disease status of an individual by processing input data using a trained machine learning algorithm model to generate an output representing the information. The disclosure also concerns a related computer program, data processing apparatus, and system, as well as a method for training a machine learning algorithm model to generate information about the disease status of an individual. The information may, for example, relate to the presence, absence or type of $M.$ $tuberculosis$ complex infection in the individual.

BACKGROUND

The World Health Organisation has stated that a diagnostic test to differentiate active tuberculosis (ATB) disease from latent tuberculosis infection (LTBI) is crucial for their aim of eradicating tuberculosis. However, no validated method currently exists to determine tuberculosis (TB) disease status.

The immune response to infection with $M.$ $tuberculosis$ is predominantly a cell mediated immune (CMI) response. As part of this response, T cells are sensitised to $M.$ $tuberculosis$ antigens. Both CD4+ and CD8+ effector T cells may be activated. $M$ $tuberculosis$ complex infection may be diagnosed in an individual by enumerating effector T cells specific for $M.$ $tuberculosis$. In particular, effector T cells may be separated from a blood sample from the individual and contacted with one or more $M.$ $tuberculosis$ antigens. Effector T cells specific for $M.$ $tuberculosis$ are stimulated by contact with the one or more antigens, and may thus be identified and enumerated.

This principle is employed by the widely-used T-SPOT.TB test. The T-SPOT.TB test is an enzyme-linked immunospot (ELISpot) based interferon gamma release assay (IGRA). The T-SPOT.TB test uses two separate panels of antigens, simulating the well-characterised $M.$ $tuberculosis$ proteins ESAT-6 and CFP10 respectively, to optimise the sensitivity of the test. The test enumerates individual activated TB-specific T cells. It is suitable for use with all patients at risk of LTBI or suspected of having TB disease, regardless of age, sex, ethnicity, therapy or immune status.

To perform the T-SPOT.TB test, peripheral blood mononuclear cells (PBMCs) are separated from a whole blood sample and washed to remove any sources of background interfering signal. The PBMCs are then counted so that a standardised cell number is used in the test. This ensures that even individuals that have a low T cell titre due to weakened immune systems (e.g. the immunocompromised and immunosuppressed) can be tested. PMBCs are then added to each of four wells of the test plate: (1) a nil control to identify non-specific cell activation; (2) TB-specific antigens, Panel A (ESAT-6 peptides); (3) TB-specific antigens, Panel B (CFP10 peptides); and (4) a positive control containing phytohaemagglutinin (PHA), a known polyclonal activator. If $M.$ $tuberculosis$-specific T cells are present, interferon gamma (INF-γ) will be produced when PMBCs are contacted with TB-specific antigens. The INF-γ is captured on a membrane present in the well. Following a colorimetric reaction, the INF-γ footprint of each responding cell can be visualised as a "spot" and counted. Spots can be counted by a number of methods, however automated methods use a dedicated ELISpot plate image reader and software (e.g. provided by Cellular Technology Ltd, Autoimmun Diagnostika GmbH). The number of spots is correlated with the number $M.$ $tuberculosis$-specific effector T cells present in the peripheral blood of the individual.

According to the package insert for the T-SPOT.TB test in the US, the test result is deemed to be positive (i.e. $M.$ $tuberculosis$ infection is deemed to be present in the individual) if the spot count in Panel A or B minus the spot count in the nil control is greater than or equal to 8 spots. The test result is deemed to be negative (i.e. $M$ $tuberculosis$ infection is deemed to be absent in the individual) if the spot count in Panel A or B minus the spot count in the nil control is less than or equal to 4 spots. The test result is deemed to be borderline and a re-test is recommended if the spot count in Panel A or B minus the spot count in the nil control is 5, 6 or 7 spots.

According to the package insert for the T-SPOT.TB test outside the US, the test result is deemed to be positive (i.e. $M.$ $tuberculosis$ infection is deemed to be present in the individual) if the spot count in Panel A or B minus the spot count in the nil control is greater than or equal to 6 spots. The test result is deemed to be negative (i.e. $M$ $tuberculosis$ infection is deemed to be absent in the individual) if the spot count in Panel A or B minus the spot count in the nil control is less than or equal to 5 spots.

Various unsuccessful attempts have been made to distinguish ATB and LTBI based on the output of the T-SPOT.TB test. In particular, attempts have been made to correlate the number of spots obtained in the antigen wells (panel A and/or panel B) with tuberculosis disease status. Wang et al. (Int J Tuberc Lung Dis, 2016, 20(4):487-493) suggested that the T-SPOT.TB test result spot count ratio of 'antigen-specific response' to 'PHA-positive control response' had utility in differentiating tuberculosis disease state. In later publications, Luo et al. (Journal of infection, 2020, 81(1): 81-89) and Wang et al. (Frontiers in Medicine, April 2020, Volume 7, Article 119) considered the potential use of ESAT-6 antigen well spot size and different PBMC cell plating concentrations for the positive control well to discriminate between ATB and LTBI.

However, it has proved challenging to reproduce the findings for either ratio of TB-antigen:PHA spot count nor ESAT-6 well mean spot size in order to differentiate ATB versus LTBI. Independent verification of the spot count (TBAg/PHA) ratio on a more diverse range of clinical samples from a different regional population found that it is not useful in differentiating ATB from LTBI. Furthermore, it is extremely difficult to accurately and reliably determine PHA well spot counts. The T cell response to the positive control (PHA) well produces hundreds of spots (see FIG. 1). Within this range, the ability to accurately count the spots (either by eye or by automatic plate imaging readers) is lost and it is very challenging to reliably evaluate the number of spots. This leads to a large margin of error for the given TBAg/PHA spot count ratio.

A more reliable diagnostic test to distinguish ATB from LTBI is therefore required.

SUMMARY

In pursuit of a more reliable diagnostic test to distinguish ATB from LTBI, the present inventors have found that a trained machine learning algorithm model may be used to glean information about the disease status of an individual based on the results of an ELISpot assay performed on a cell sample obtained from the individual. In particular, data that is derived from or consists of image data representing the visible read-out of the ELISpot assay may be processed using the trained machine learning algorithm model to generate an output that represents information about the disease status of the individual, such as the type of *M. tuberculosis* complex infection present in the individual. It is not necessary to count spots in order to obtain the information, and so a potential source of error is removed. Furthermore, the inventors' findings allow existing diagnostic tests (e.g. the T-SPOT.TB assay) to be used in new ways (e.g. to provide information about the type of disease, rather than its mere presence or absence in the individual).

Accordingly, the disclosure provides a method of obtaining information about the disease status of an individual, the method comprising: (a) receiving input data that comprises data derived from or consisting of image data of each of at least two wells of an enzyme-linked immunospot (ELISpot) assay performed on a cell sample obtained from the individual; and (b) processing the input data using a trained machine learning algorithm model to generate an output representing information about the disease status of the individual.

The disclosure also provides:

a method of using a trained machine learning algorithm model to characterise a *M. tuberculosis* complex infection present in an individual as active or latent, the method comprising: (a) receiving input data that comprises data derived from or consisting of image data of each of at least two wells of an enzyme-linked immunospot (ELISpot) assay for *M. tuberculosis* complex infection performed on a cell sample obtained from the individual; and (b) processing the input data using the trained machine learning algorithm model to generate an output representing information which characterises the *M. tuberculosis* complex infection as active or latent;

a method of training a machine learning algorithm model to generate information about the disease status of an individual, the method comprising training the machine learning algorithm model using a plurality of training data units, each training data unit comprising (i) input data that comprises data derived from or consisting of image data of each of at least two wells of an enzyme-linked immunospot (ELISpot) assay performed on a cell sample obtained from a respective training individual and (ii) data representing information about the disease status of the respective training individual;

a computer program comprising instructions that, when executed by a computer system, instruct the computer system to perform the method of the disclosure;

a data processing apparatus comprising a processor configured to perform the method of the disclosure; and a system for obtaining information about the disease status of an individual, comprising: the data processing apparatus of the disclosure; and an image capturing device configured to capture the image data.

DETAILED DESCRIPTION

Figure 1:
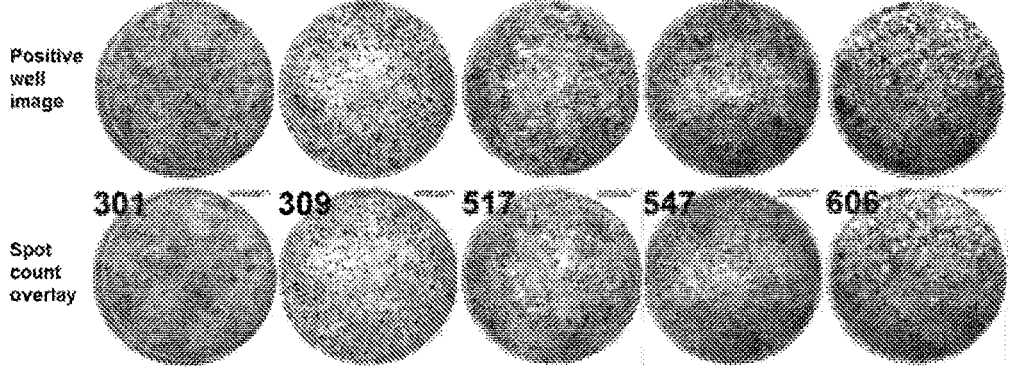
FIG. 1: Challenge of PHA spot counting. Five positive control well images from T-SPOT.TB test samples with corresponding ELISpot reader software spot counts.

It is to be understood that different applications of the disclosed methods and products may be tailored to the specific needs in the art. It is also to be understood that the terminology used herein is for the purpose of describing particular embodiments of the disclosure only, and is not intended to be limiting.

In addition, as used in this specification and the appended claims, the singular forms "a", "an", and "the" include plural referents unless the content clearly dictates otherwise. Thus, for example, reference to "a cell" includes "cells", reference to "an image" includes two or more such images, reference to "an antigen" includes two or more such antigens, and the like.

All publications, patents and patent applications cited herein, whether supra or infra, are hereby incorporated by reference in their entirety.

Method for Obtaining Information about the Disease Status of an Individual

The disclosure provides a method of obtaining information about the disease status of an individual, the method comprising: (a) receiving input data that comprises data derived from or consisting of image data of each of at least two wells of an enzyme-linked immunospot (ELISpot) assay performed on a cell sample obtained from the individual; and (b) processing the input data using a trained machine learning algorithm model to generate an output representing information about the disease status of the individual.

Information about the Disease Status of the Individual

The information about the disease status of the individual may comprise information about the presence of a disease in the individual. The information about the disease status of the individual may comprise information about the absence of a disease in the individual.

The information about the disease status of the individual may comprise information that characterises a disease present in the individual. For example, the information may characterise the disease as being of a particular subtype, state or stage. For instance, the information may characterise an infectious disease present in the individual as an active infection. That is, the information about the disease status of the individual may be information about the infectious disease status of the individual. The information may characterise an infectious disease present in the individual as a latent infection. The infectious disease may, for example, be *M. tuberculosis* complex infection. Active *M. tuberculosis* complex infection (ATB) and latent *M. tuberculosis* complex infection (LTBI) are discussed below in connection with a method of characterising *M tuberculosis* complex infection.

The information about the disease status of the individual may comprise information that characterises the risk of the individual contracting a disease. For example, the information may comprise information about the presence or absence of an adaptive immune response that may be capable of protecting against the disease. The information may comprise information about the strength an adaptive immune response present in the individual that may be capable of protecting against the disease. The information may comprise information about the presence or absence of an adaptive immune response that may contribute to the pathogenesis of the disease. The information may comprise information about the strength an adaptive immune response present in the individual that may contribute to the pathogenesis of the disease. The adaptive immune response may be a T cell response, such as a CD4+ T cell response or a CD8+ T cell response. The adaptive immune response may be a B cell response.

The disease may be any disease in which an adaptive immune response is mounted. In an adaptive immune response, binding of antigen to an antigen receptor on the surface of an antigen-specific immune cell may result in the secretion of an immune effector molecule that is detectable using an ELISpot assay. For example, binding of antigen to a T cell receptor (TCR) on the surface of a T cell may result in the secretion of a cytokine, chemokine, or cytolytic molecule. Binding of antigen to a B cell receptor (BCR) on the surface of a B cell may result in the secretion of an antibody. Accordingly, the adaptive immune response may be a T cell response, such as a CD4+ T cell response or a CD8+ T cell response. The adaptive immune response may be a B cell response.

Preferably, the disease is an infectious disease. For example, the disease may be a bacterial, viral or protozoal infection. Preferably, the disease is a bacterial infection. More preferably, the disease is *M. tuberculosis* complex infection. Accordingly, the information about the disease status of the individual may comprise information about the presence of bacterial infection (such as *M. tuberculosis* complex infection) in the individual. The information about the disease status of the individual may comprise information about the absence of bacterial infection (such as *M. tuberculosis* complex infection) in the individual. The information about the disease status of the individual may comprise information about the nature of a bacterial infection (such as *M. tuberculosis* complex infection) present in the individual. The nature of the bacterial infection may, for example, be latent infection. The nature of the bacterial infection may, for example, be active infection.

The disease may be a viral infection. Preferably, the viral infection is a coronavirus infection, such as SARS-CoV-2 infection. Accordingly, the information about the disease status of the individual may comprise information about the presence of viral infection (such as SARS-CoV-2 infection) in the individual. The information about the disease status of the individual may comprise information about the absence of viral infection (such as SARS-CoV-2 infection) in the individual. The information about the disease status of the individual may comprise information about the presence or absence of cell-mediated immunity to the viral infection (such as SARS-CoV-2 infection). For instance, the information about the disease status of the individual may comprise information about the presence or absence of a T cell response to the viral infection (such as SARS-CoV-2 infection). The information about the disease status of the individual may comprise information about the strength of a T cell response present in the individual to the viral infection (such as SARS-CoV-2 infection). The cell mediated immunity may be protective against the viral infection. The T cell response may be protective against the viral infection.

The viral infection may be a cytomegalovirus (CMV) infection. CMV can affect individuals with weaknesses in their T cell response and it is therefore an important and common cause of morbidity and mortality in solid organ and hematopoietic stem cell transplant recipients. Measuring the strength of T cell responses to CMV specific antigens may assist clinicians in monitoring anti-viral prophylaxis and evaluating patients at risk from CMV disease. Accordingly, the information about the disease status of the individual may comprise information about the presence or absence of cell-mediated immunity to the CMV infection. For instance, the information about the disease status of the individual may comprise information about the presence or absence of a T cell response to the CMV infection. The information about the disease status of the individual may comprise information about the strength of a T cell response present in the individual to the CMV infection. The cell mediated immunity may be protective against the CMV infection. The T cell response may be protective against the CMV infection.

The disease may, for example, be an autoimmune, allergic or immune-mediated disease. The immune-mediated disease may, for example, be transplant rejection. Antibodies specific for a donor antigen may drive a rejection event in an individual receiving a transplant. Measuring the strength of B cell responses to donor specific antigens may assist clinicians evaluating patients at risk from transplant rejection. Accordingly, the information about the disease status of the individual may comprise information about the presence or absence of a B cell response to a donor specific antigen. The information about the disease status of the individual may comprise information about the strength of a B cell response present in the individual to a donor specific antigen. The B cell response may be capable of precipitating transplant rejection.

The disease may, for example, be cancer.

Preferably, the individual is a human individual. Alternatively, the individual may be a non-human animal, such as a non-human mammal. For instance, the individual may be a pet mammal (such as a cat, a dog, a horse, a rabbit or a guinea pig), a commercially farmed mammal (such as an ox, a sheep, a goat or a pig), or a laboratory mammal, (such as a mouse or a rat). The individual may be an infant, a juvenile or an adult. The individual may be known to have the disease, or suspected to have the disease. The individual may undergo screening for the disease.

Input Data

The input data comprises data derived from or consisting of image data of each of at least two wells of an ELISpot assay performed on a cell sample obtained from the individual. For example, the input data may comprise data derived from or consisting of image data of each of at least three wells, at least four, at least five, at least six, at least seven, at least eight, at least nine, or at least 10 wells of an ELISpot assay performed on a cell sample obtained from the individual. The cell sample may, for example, consist of or be derived from a blood sample. Preferably, the cell sample comprises peripheral blood mononuclear cells (PBMCs). The PBMCs may comprise T cells and/or B cells, and/or NK cells. Preferably, the PBMCs comprise T cells.

The input data may comprise data that consists of image data of each of at least two wells of an ELISpot assay performed on a cell sample obtained from the individual. The input data may comprise data that is derived from image data of each of at least two wells of an ELISpot assay performed on a cell sample obtained from the individual. For example, the input data may comprise data that is derived by formatting the image data. Formatting may, for example, comprise adjusting the size of an image comprised in the image data. Formatting may, for example, comprise adjusting the resolution of an image comprised in the image data. The size and/or resolution may be adjusted in order to bring the format of image data into conformity with the format of image data used to train the trained machine learning algorithm model.

ELISpot assays are well-known in the art. The ELISpot is an immunoassay that measures the frequency of protein secreting cells in a sample at the single-cell level. Cells from the cell sample are cultured in one or more wells of an assay plate. Each well comprises a surface coated with a capture antibody specific for the secreted protein of interest. A different stimulus regime may be applied to each of the one or more well, for example to provide test wells and control wells. Proteins that are secreted by the cells are captured by the capture antibody. After an appropriate incubation time, cells are removed and the secreted protein is detected using a detection antibody that is directly or indirectly conjugated with an enzyme. Upon contact of the enzyme with a substrate forming precipitating product, visible spots from on the surface. Each spot corresponds to an individual protein-secreting cell.

The secreted protein may, for example, be a cytokine. Preferably, the cytokine is interferon gamma (IFN-γ). In other words, the ELISpot assay may be an interferon gamma release assay (IGRA). For example, the ELISpot assay may be a T-SPOT.TB assay. The T-SPOT.TB assay is well-known in the art, and described above. The ELISpot assay may, for example, be a T-SPOT.COVID assay.

Like the T-SPOT.TB test, the T-SPOT.COVID test is an enzyme-linked immunospot (ELISpot) based interferon gamma release assay (IGRA). The T-SPOT. COVID test uses two separate panels of antigens, simulating the well-characterised SARS-CoV-2 spike (S) and nucleocapsid (N) proteins respectively, to optimise the sensitivity of the test. The test enumerates individual activated SARS-CoV-2-specific T cells. To perform the T-SPOT.COVID test, peripheral blood mononuclear cells (PBMCs) are separated from a whole blood sample and washed to remove any sources of background interfering signal. The PBMCs are then counted so that a standardised cell number is used in the test. This ensures that even individuals that have a low T cell titre due to weakened immune systems (e.g. the immunocompromised and immunosuppressed) can be tested. PMBCs are then added to each of four wells of the test plate: (1) a nil control to identify non-specific cell activation; (2) SARS-CoV-2-specific antigens, Panel A (spike peptides); (3) SARS-CoV-2-specific antigens, Panel B (nucleocapsid peptides); and (4) a positive control containing phytohaemagglutinin (PHA), a known polyclonal activator. If SARS-CoV-2-specific T cells are present, interferon gamma (INF-γ) will be produced when PMBCs are contacted with SARS-CoV-2-specific antigens. The INF-γ is captured on a membrane present in the well. Following a colorimetric reaction, the INF-γ footprint of each responding cell can be visualised as a "spot" and counted, as for T-SPOT.TB. The test result may be deemed to be positive (i.e. a T cell response to SARS-CoV-2 is deemed to be present) if the spot count in Panel A or B minus the spot count in the nil control is greater than or equal to 8 spots. The test result is deemed to be negative (i.e. a T cell response to SARS-CoV-2 is deemed to be absent) if the spot count in Panel A or B minus the spot count in the nil control is less than or equal to 4 spots. The test result is deemed to be borderline and a re-test is recommended if the spot count in Panel A or B minus the spot count in the nil control is 5, 6 or 7 spots.

Accordingly, a different stimulus regime may be applied to the cell sample in each of the at least two wells to which the image data relates. Each stimulus regime may, for example be selected from (a) no stimulus; (b) a known activator of cells comprised in the sample; and (c) a potential activator of cells comprised in the sample. A well to which no stimulus is applied may provide a negative control for the assay. A well to which a known activator of cells comprised in the sample is applied may provide a positive control for the assay. A well to which a potential activator of cells comprised in the sample is applied may act as a test well.

The identity of the known activator (b) will depend on the type of cells comprised in the sample. For example, the cell sample may preferably comprise T cells. In this case, the known activator (b) may be a known T cell activator, such as phytohaemagglutinin (PHA).

Preferably, the potential activator (c) comprises an antigen. The antigen may, for example, be a bacterial antigen or a viral antigen. The antigen may, for example, be selected to match the disease about whose status information is being obtained. For instance, in one aspect, the antigen is preferably a bacterial antigen. More preferably, the antigen is a *M. tuberculosis* antigen. The *M. tuberculosis* antigen may, for example, comprise an ESAT-6 peptide or a CFP10 peptide. The *M. tuberculosis* antigen may, for example, comprise a panel of ESAT-6 peptides that simulate ESAT-6 protein, such as panel A used in the T-SPOT.TB assay. The *M. tuberculosis* antigen may, for example, comprise a panel of CFP10 peptides that simulate CFP10 protein, such as panel B used in the T-SPOT.TB assay. In another aspect, the antigen is preferably a viral antigen. More preferably, the antigen is a SARS-CoV-2 antigen. The SARS-CoV-2 antigen may, for example, comprise (a) a spike antigen (S) peptide, (b) a nucleocapsid (N) peptide, (c) a matrix protein (M) peptide, and/or (d) an envelope protein (E) peptide. For example, the SARS-CoV-2 antigen may comprise (i); (ii); (iii); (iv); (i) and (ii); (i) and (iii); (i) and (iv); (ii) and (iii); (ii) and (iv); (iii) and (iv); (i), (ii) and (iii); (i), (ii) and (iv); ((i); (iii) and (iv); (ii), (iii) and (iv); or (i), (ii), (iii) and (iv). The SARS-CoV-2 antigen may, for example, comprise a panel of spike (S) peptides that simulate the spike (S) protein, such as panel A used in the T-SPOT.COVID assay. The SARS-CoV-2 antigen may, for example, comprise a panel of nucleocapsid (N) peptides that simulate the nucleocapsid (N) protein, such as panel B used in the T-SPOT.COVID assay.

The image data may be of each of two wells of the ELISpot assay. Each of the two wells may be selected from (i) a well to which no stimulus is applied, (ii) a well to which a known activator of cells comprised in the sample is applied, and (iii) a well to which a potential activator of cells comprised in the sample is applied. The image data may be of (i) and (ii); (i) and (iii); or (ii) and (iii). Each of the two wells may be selected from (1) a well to which no stimulus is applied, (2) a well to which a known activator of cells comprised in the sample is applied, (3) a well to which a first potential activator of cells comprised in the sample is applied, and (4) a well to which a second potential activator of cells comprised in the sample is applied. The image data may be of (1) and (2); (1) and (3); (1) and (4); (2) and (3); (2) and (4); (3) and (4).

The image data may be of each of three wells of the ELISpot assay. Each of the three wells may be selected from (i) a well to which no stimulus is applied, (ii) a well to which a known activator of cells comprised in the sample is applied, and (iii) a well to which a potential activator of cells comprised in the sample is applied. The image data may therefore be of (i), (ii), and (iii). Each of the three wells may be selected from (1) a well to which no stimulus is applied, (2) a well to which a known activator of cells comprised in the sample is applied, (3) a well to which a first potential activator of cells comprised in the sample is applied, and (4) a well to which a second potential activator of cells comprised in the sample is applied. The image data may be of (1), (2) and (3); (1), (2) and (4); (1), (3) and (4); or (2), (3) and (4).

The image data may be of each of four wells of the ELISpot assay. Each of the four wells may be selected from (1) a well to which no stimulus is applied, (2) a well to which a known activator of cells comprised in the sample is applied, (3) a well to which a first potential activator of cells comprised in the sample is applied, and (4) a well to which a second potential activator of cells comprised in the sample is applied. The image data may be of (1), (2), (3) and (4).

In the T-SPOT.TB test, each of the at least two wells is selected from (1) a well to which no stimulus is applied, (2) a well to which a known activator of cells comprised in the sample is applied, (3) a well to which a first potential activator of cells comprised in the sample is applied, and (4) a well to which a second potential activator of cells comprised in the sample is applied. The known activator of (2) is PHA. The first potential activator of (3) is a panel of ESAT-6 peptides that simulate ESAT-6 protein. The second potential activator of (4) is a panel of CFP10 peptides that simulate CFP10 protein.

In the T-SPOT.COVID test, each of the at least two wells is selected from (1) a well to which no stimulus is applied, (2) a well to which a known activator of cells comprised in the sample is applied, (3) a well to which a first potential activator of cells comprised in the sample is applied, and (4) a well to which a second potential activator of cells comprised in the sample is applied. The known activator of (2) is PHA. The first potential activator of (3) is a panel of spike (S) peptides that simulate spike (S) protein. The second potential activator of (4) is a panel of nucleocapsid (N) peptides that simulate nucleocapsid (N) protein.

The input data may comprise one or more individual data units. Each individual data unit may relate to the same type of data. Each individual data unit may, for example, be derived from or consist of image data, such as image data of one or more wells of the ELISpot assay. In a first aspect, the input data may comprise plural individual data units, each individual data unit being derived from or consisting of image data of a different respective one of the at least two wells. Essentially, the input data may comprise multiple units of image data, each relating to a different well of the ELISpot assay. In a second aspect, the input data may comprise data derived from or consisting of image data representing a composite image containing images of all of the at least two wells. Essentially, the input data may comprise a single unit of image data that relates to multiple different wells of the ELISpot assay. The first and second aspects are not mutually exclusive. That is, the input data may comprise (a) plural individual data units, each individual data unit being derived from or consisting of image data of a different respective one of the at least two wells; and (b) data derived from or consisting of image data representing a composite image containing images of all of the at least two wells.

The input data may comprise two or more individual data units each relating to a different type of data. For example, one of the two or more individual data units may be derived from or consist of image data, and one of the two or more individual data units may not be derived from or consist of image data. For example, in addition to the data derived from or consisting of image data of each of at least two wells of the ELISpot assay, the input data may comprise data that is neither derived from nor consists of image data of a well of the ELISpot assay.

The data that is neither derived from nor consists of image data of a well of the ELISpot assay may comprise clinical or epidemiological data relating to the individual. For instance, clinical or epidemiological data may include HIV status, age of individual and an individual's country of origin.

The data that is neither derived from nor consists of image data of a well of the ELISpot assay may comprise data relating to the cell sample. Preferably, the data relating to the cell sample comprises data obtained from the cell sample prior to or during performance of the ELISpot assay. That is, the data that is neither derived from nor consists of image data of a well of the ELISpot assay may be data that is routinely collected prior to or during one or more steps of the ELISpot assay, such as data that is required to ensure that the ELISpot assay is performed correctly or gives reliable results. For instance, the data obtained during performance of the ELISpot assay may be derived from or consist of the number of cells comprised in the cell sample. Preferably, the data obtained during performance of the ELISpot assay may be derived from or consist of the number of PBMCs comprised in the cell sample, e.g. the number of PBMC (cell s/mL) recovered from a whole blood sample.

Methods for determining the number of cells or PBMCs in a sample are known in the art. The number of cells (such as PBMCs) in a sample may, for example, be determined manually, for example using a haemocytometer. The number of cells (such as PBMCs) in a sample may, for example, be determined using a commercially-available automated cell counter. The automated cell counter may, for example, determine the number of cells (such as PBMCs) in a sample by measuring optical and/or electrical impedance, for instance as the sample passes through a chamber of the counter. The number of cells (such as PBMCs) in a sample may, for example, be determined using flow cytometry.

The data relating to the cell sample may comprise data relating to expression of markers by cells comprised in the sample. For example, the data may relate to expression of the T cell marker CD3 by cells comprised in the sample. The data may relate to expression of CD4 by cells (such as T cells) comprised in the sample. The data may relate to expression of CD8 by cells (such as T cells) comprised in the sample. The data may relate to expression of an activation marker (such as HLA-DR, CD38, CD127 or CD154) by cells (such as T cells) comprised in the sample. Methods of determining marker expression are known in the art. Marker expression may, for example, be assessed using flow cytometry to determine the mean fluorescence intensity (MFI) of expression of the marker by cells comprised in the sample. Marker expression may, for example, be assessed using flow cytometry to determine the percentage of cells comprised in the sample that express the marker.

The data that is neither derived from nor consists of image data of a well of the ELISpot assay may comprise data relating to the concentration of analytes in the well. The analyte may, for example, be a cytokine, (such as, e.g. IL-2, TNF-alpha) secreted into the supernatant by the cells present in the well. Methods for determining analyte concentration are known in the art and include, for example, enzyme-linked immunosorbent assay (ELISA).

Trained Machine Learning Algorithm Model

The input data is processed using a trained machine learning algorithm model in order to generate an output representing information about the disease status of the individual. The machine learning algorithm model may comprise a neural network. Preferably, the neural network is a convolutional neural network.

The machine learning algorithm model may perform a single processing step on the input data in order to produce the output. Alternatively, the machine learning algorithm model may perform a plurality of processing steps on the input data in order to produce the output. One or more of the plurality of processing steps may produce a sub-output that is used by the machine learning algorithm model in the next processing step. That is, two or more of the plurality of processing steps may be performed in series. Two or more of the plurality of processing steps may be performed in parallel.

Any of the processing steps may comprise a classification step. The classification step may be a binary classification step that produces an output associated with one of two categories. For example, the classification step may produce an output associated with the presence of (1) ATB or (2) LTBI. The classification step may produce an output associated with (1) the presence of *M. tuberculosis* complex infection or (2) the absence of *M. tuberculosis* complex infection. The classification step may produce an output associated with one of more than two categories. For example, the classification step may produce an output associated with (1) ATB, (2) LTBI or (3) the absence of *M. tuberculosis* complex infection.

Figure 16:
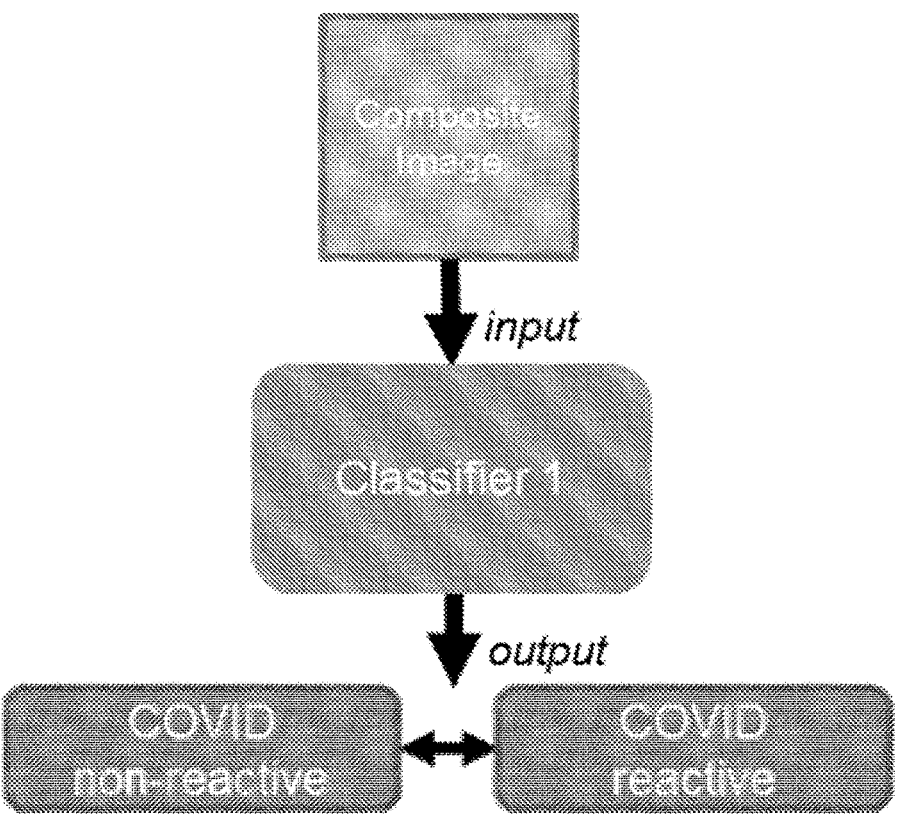
FIG. 16: System diagram showing the steps comprised in an exemplary trained machine learning algorithm model, reflective of T-SPOT.COVID classifier model m12.

FIGS. 3 to 9, 16 and 19 show the steps comprised in exemplary machine learning algorithm models. Each of FIGS. 3 to 9 and 19 relate to obtaining information about the *M. tuberculosis* status of an individual using input data relating to a T-SPOT.TB assay performed on a cell sample obtained from the individual. FIG. 16 relates to obtaining information about the SARS-CoV-2 status of an individual using input data relating to a T-SPOT.COVID assay performed on a cell sample obtained from the individual. However, the particular disease and assay considered in FIGS. 3 to 9, 16 and 19 is merely illustrative. The skilled person would recognise that systems comprising similar steps to those illustrated could be used to obtain information about the status of other diseases, using input data relating to other ELISpot assays.

In FIG. 3A, the machine learning algorithm model receives input data comprising data derived from or consisting of image data representing a composite image containing images of all of the at least two wells. A single classification step is used to produce an output associated with (1) ATB, (2) LTBI or (3) the absence of *M. tuberculosis* complex infection. The system shown in FIG. 3A may therefore be used to simultaneously determine the presence or absence of *M. tuberculosis* complex infection in an individual and, if *M. tuberculosis* complex infection is present, to characterise it as ATB or LTBI.

In FIG. 3B, the machine learning algorithm model receives input data comprising data derived from or consisting of image data representing a composite image containing images of all of the at least two wells. A first classification step is used to produce an output associated with the presence or absence of *M. tuberculosis* complex infection. If *M tuberculosis* complex infection is present, the input data is processed again using a second classification step, to characterise the *M. tuberculosis* complex infection as ATB or LTBI.

In FIG. 4A, the machine learning algorithm model receives input data comprising data derived from or consisting of image data representing a composite image containing images of all of the at least two wells. A single classification step is used to produce an output associated with the presence or absence of *M. tuberculosis* complex infection. The system shown in FIG. 4A may therefore be used to determine the presence or absence of *M. tuberculosis* complex infection in an individual. The system shown in FIG. 4A is representative of the structure of model m11 considered in the Examples. The system/model may be used to interpret input data comprising data derived from or consisting of image data representing a composite image containing images of all of at least two wells of a TB-specific ELISpot assay (such as a TB-IGRA ELISpot assay, e.g. a T-SPOT.TB test) in order to output a positive result indicative of the presence of *M. tuberculosis* complex infection or a negative result indicative of the absence of *M. tuberculosis* complex infection. In essence, the system/model can be used to "read" the TB-specific ELISpot assay.

In FIG. 4B, the machine learning algorithm model receives input data comprising data derived from or consisting of image data representing a composite image containing images of all of the at least two wells. A single classification step is used to produce an output associated with (1) ATB or (2) LTBI. The system shown in FIG. 4B may therefore be used to characterise *M. tuberculosis* complex infection present in an individual as ATB or LTBI. The system shown in FIG. 4B is representative of the structure of models m6 to m10 considered in the Examples.

The systems shown in FIGS. 4A and 4B may be integrated or sequentially combined to arrive at the system that is capable of determining the presence or absence of *M. tuberculosis* complex infection and, if *M. tuberculosis* complex infection is present, characterising *M. tuberculosis* complex infection as latent or active. As set out above, the system shown in FIG. 4A (which is representative of model m11) may be used to "read" a TB-specific ELISpot assay in order to output a positive result indicative of the presence of *M. tuberculosis* complex infection or a negative result indicative of the absence of *M. tuberculosis* complex. Input data giving rise to a positive result may be automatically processed by the system shown in FIG. 4B (which is representative of models m6 to m10) to characterise the *M. tuberculosis* complex infection present in the individual as ATB or LTBI. The resultant integrated or combined system may preferably be represented by FIG. 3B. Preferably, model m11 is integrated or sequentially combined with model m10.

Figure 5:
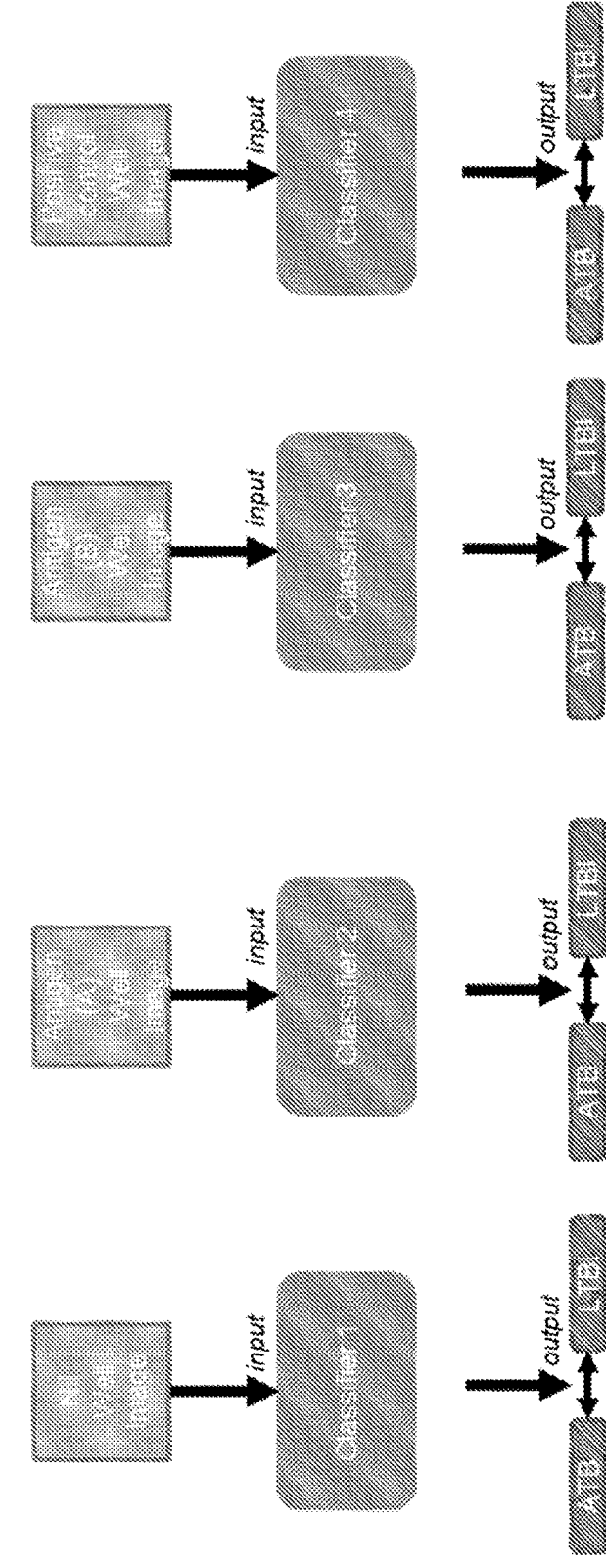

In FIG. 5, each panel relates to a separate, single well system. In each system, the machine learning algorithm model receives input data that comprises data derived from or consisting of image data of just one well of the T-SPOT.TB assay. From left to right, the well for each system is: a nil control to identify non-specific cell activation; TB-specific antigens, Panel A (ESAT-6 peptides); TB-specific antigens, Panel B (CFP10 peptides); and a positive control containing phytohaemagglutinin (PHA). In each system, a single classification step is used to produce an output associated with (1) ATB or (2) LTBI. The systems shown left to right in FIG. 5 are respectively representative of the structure of models m1 to m4 considered in the Examples.

Figure 6:
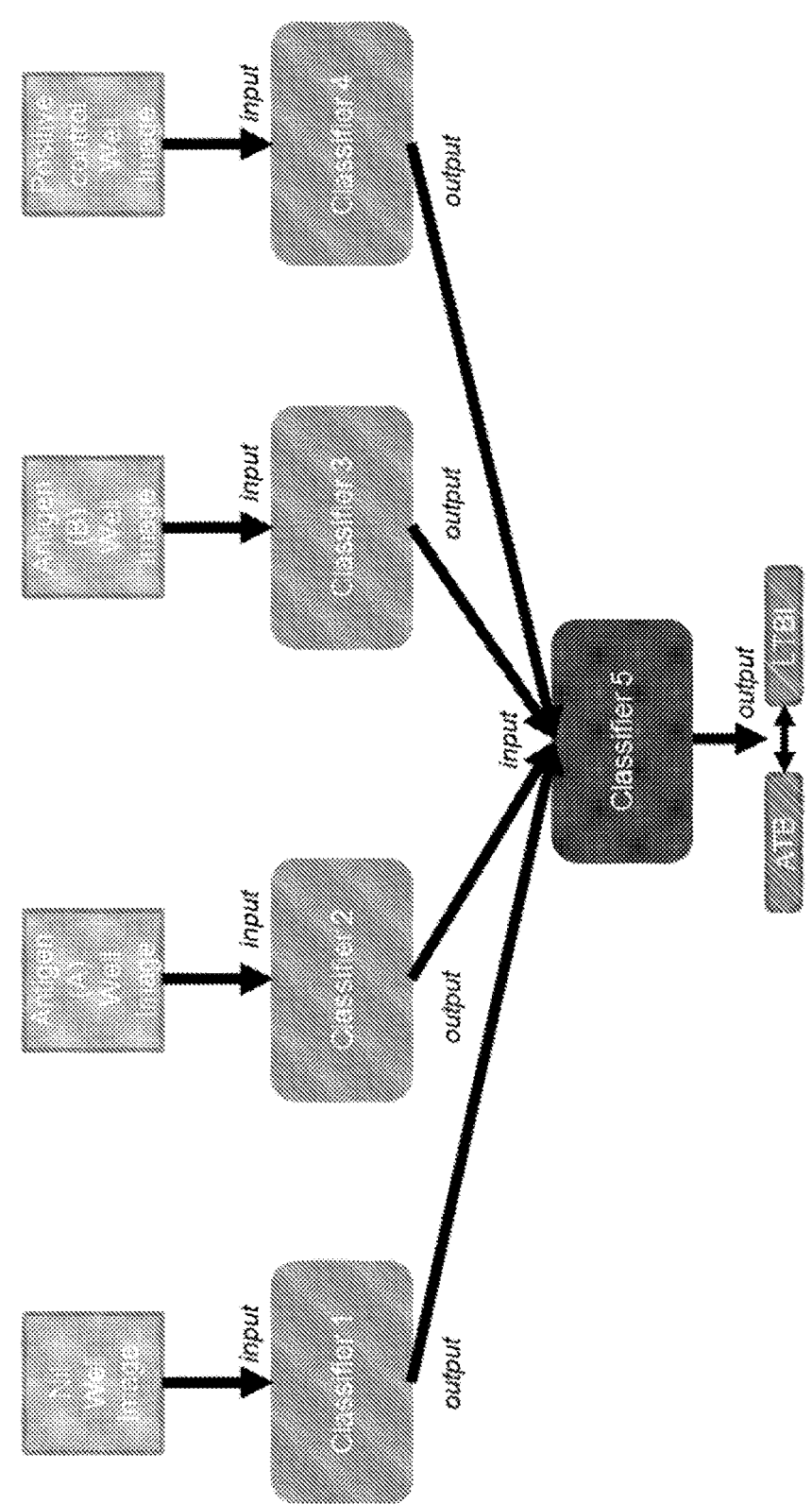

In FIG. 6, the machine learning algorithm model receives input data comprising plural individual data units, each individual data unit being derived from or consisting of image data of a different respective one of the wells of the T-SPOT.TB assay. From left to right, the well is: a nil control to identify non-specific cell activation; TB-specific antigens, Panel A (ESAT-6 peptides); TB-specific antigens, Panel B (CFP10 peptides); and a positive control containing PHA. Each individual data unit is processed using a different first classification step (classifiers 1 to 4). The output of each first classification step may be, for example, a value associated with probability of the presence of ATB or LTBI in the individual. The output of each first classification step is used in a common second classification step (classifier 5). The second classification step may, for example, apply a weighting to the output of each first classification step. The second classification step produces an output associated with (1) ATB or (2) LTBI.

Figure 7:
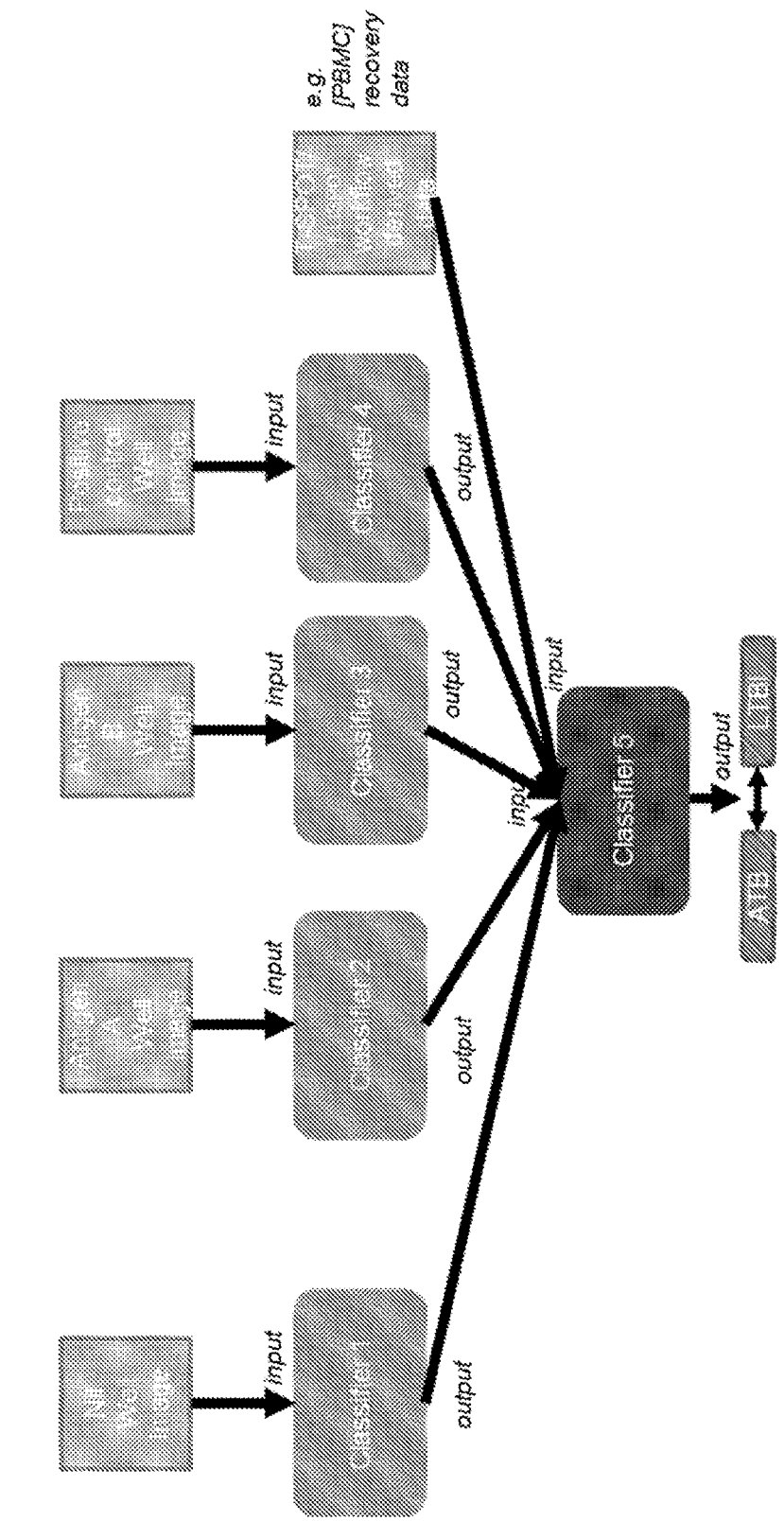
Figure 8:
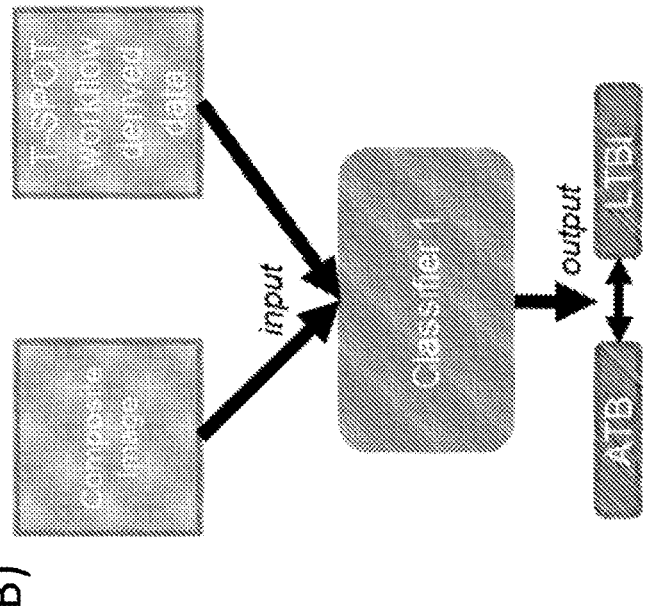
Figure 8:
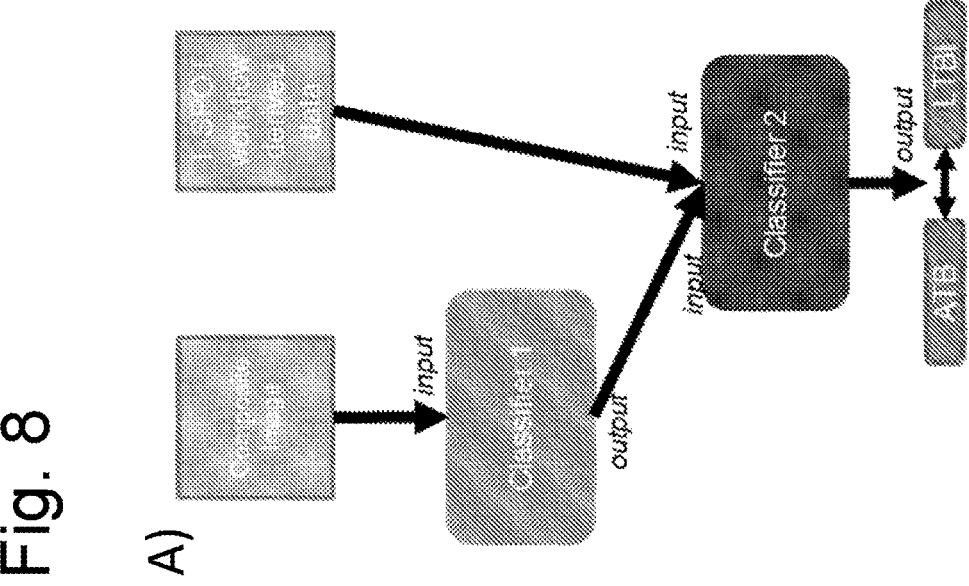
Figure 9:
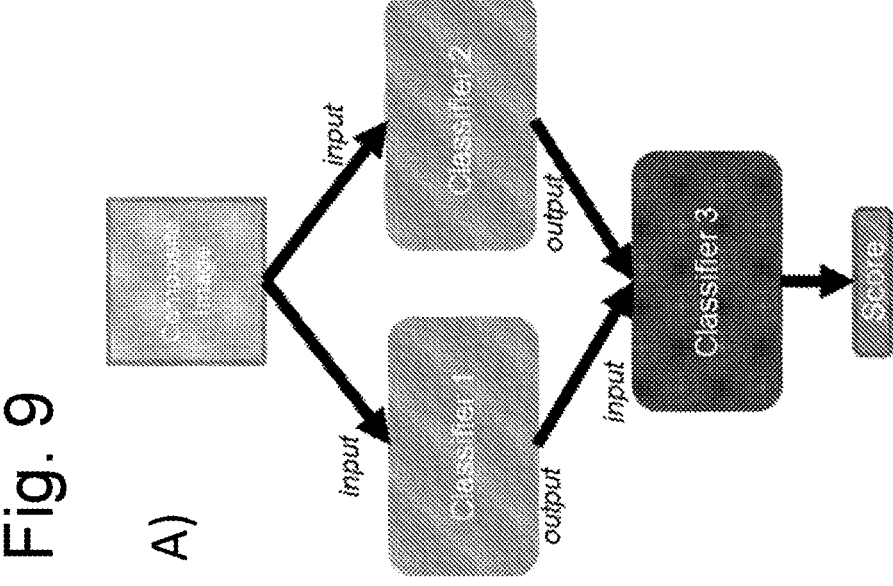
Figure 9:
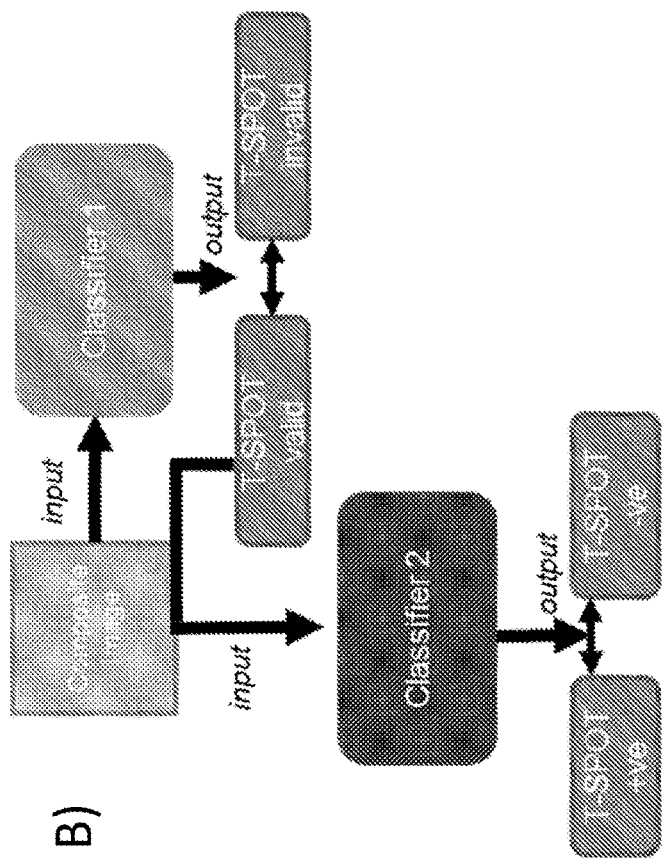

The system shown in FIG. 7 is similar to that shown in FIG. 6, except that there is an additional input to the second classification step. As well as the output of each first classification step, the second classification step receives input data that is obtained during performance of the ELISpot assay, such as data derived from or consisting of the number of PBMCs comprised in the cell sample.

In FIG. 8A, a first classification step (classifier 1) of the machine learning algorithm model receives input data comprising data derived from or consisting of image data representing a composite image containing images of all of the at least two wells. The output of the first classification step may be, for example, a value associated with probability of the presence of ATB or LTBI in the individual. A second classification step (classifier 2) receives (i) the output of the first classification step and (ii) input data that is obtained during performance of the ELISpot assay, such as data derived from or consisting of the number of PBMCs comprised in the cell sample. The second classification step produces an output that characterises the *M. tuberculosis* complex infection as ATB or LTBI.

In FIG. 8B, a single classification step (classifier 1) of the machine learning algorithm model receives input data comprising (i) data derived from or consisting of image data representing a composite image containing images of all of the at least two wells; and (ii) data that is obtained during performance of the ELISpot assay, such as data derived from or consisting of the number of PBMCs comprised in the cell sample. The single classification step produces an output that characterises the *M. tuberculosis* complex infection as ATB or LTBI.

FIG. 9A provides a general representation of an ensemble classifier. In FIG. 9A, input data comprising data derived from or consisting of image data representing a composite image containing images of all of the at least two wells is processed using parallel classification steps (classifiers 1 and 2). Each of the parallel classification steps processes the input data in a different way. Each of the parallel classification steps may, for example, comprise a machine learning algorithm model that has been trained in a different way. Each of the parallel classification steps may, for example, comprise a different type trained machine learning algorithm model, such as a different type of neural network. The output of each of the parallel classification steps may be, for example, a value associated with probability of the presence of ATB or LTBI in the individual. The output of each of the parallel classification steps is processed by a further classification step (classifier 3). The further classification step produces an output that, for example, (i) is associated with (1) ATB, (2) LTBI or (3) the absence of *M. tuberculosis* complex infection, or (ii) characterises the *M. tuberculosis* complex infection as ATB or LTBI. In FIG. 9B, the machine learning algorithm model receives input data comprising data derived from or consisting of image data representing a composite image containing images of all of the at least two wells. A first classification step is used to produce an output associated with the validity or invalidity of the T-SPOT.TB test. A valid T-SPOT.TB test is one that shows response in the positive control (PHA well) and a minimal response in the nil control well. For example, for a T-SPOT.TB test to be valid, the positive control well (PHA well) may be required to have 20 or more spots while the nil control well may be required to have 10 spots or fewer. If the T-SPOT.TB test is valid, the input data is processed again using a second classification step, to produce an output associated with the presence or absence of *M. tuberculosis* complex infection. The second classification step may comprise the system shown in FIG. 4A (which is representative of model m11).

In FIG. 16, the machine learning algorithm model receives input data comprising data derived from or consisting of image data representing a composite image containing images of all of the at least two wells. A single classification step is used to produce an output associated with the presence or absence of T cells reactive to SARS-CoV-2. The system shown in FIG. 16 may therefore be used to determine the presence or absence of T cells reactive to SARS-CoV-2 in an individual. The system shown in FIG. 16 is representative of the structure of model m12 considered in the Examples. The system/model may be used to interpret input data comprising data derived from or consisting of image data representing a composite image containing images of all of at least two wells of a SARS-CoV-2-specific ELISpot assay (such as a SARS-CoV-2-IGRA ELISpot assay, e.g. a T-SPOT.COVID test) in order to output a positive result indicative of the presence of T cells reactive to SARS-CoV-2 or a negative result indicative of the absence of T cells reactive to SARS-CoV-2. In essence, the system/model can be used to "read" the SARS-CoV-2-specific ELISpot assay.

In FIG. 19A, the machine learning algorithm model receives input data comprising data derived from or consisting of image data representing a composite image containing images of two wells of an ELISpot assay that comprises four wells: (1) a well to which no stimulus is applied, (2) a well to which a known activator of cells comprised in the sample is applied, (3) a well to which a first potential activator of cells comprised in the sample is applied, and (4) a well to which a second potential activator of cells comprised in the sample is applied. In FIG. 19A, the exemplary ELISpot assay is a IGRA ELISpot assay, specifically a T-SPOT.TB test which comprises the following four wells: from (1) a well to which no stimulus is applied, (2) a well to which PHA is applied, (3) a well to which a panel of ESAT-6 peptides that simulate ESAT-6 protein is applied, and (4) a well to which a panel of CFP10 peptides that simulate CFP10 protein is applied. A single classification step is used to produce an output associated with (1) ATB or (2) LTBI. The system shown in FIG. 19A may therefore be used to characterise *M. tuberculosis* complex infection present in an individual as ATB or LTBI. The system shown in FIG. 19A is representative of the structure of models m13 to m18 considered in the Examples, in which the two wells are:

(1) and (3) for m13;
(1) and (4) for m14;
(1) and (2) for m15;
(3) and (4) for m16;
(2) and (3) for m17; and
(2) and (4) for m18.

In FIG. 19B, the machine learning algorithm model receives input data comprising data derived from or consisting of image data representing a composite image containing images of three wells of an ELISpot assay that comprises four wells: (1) a well to which no stimulus is applied, (2) a well to which a known activator of cells comprised in the sample is applied, (3) a well to which a first potential activator of cells comprised in the sample is applied, and (4) a well to which a second potential activator of cells comprised in the sample is applied. In FIG. 19B, the exemplary ELISpot assay is a IGRA ELISpot assay, specifically a T-SPOT.TB test which comprises the following four wells: from (1) a well to which no stimulus is applied, (2) a well to which PHA is applied, (3) a well to which a panel of ESAT-6 peptides that simulate ESAT-6 protein is applied, and (4) a well to which a panel of CFP10 peptides that simulate CFP10 protein is applied. A single classification step is used to produce an output associated with (1)

ATB or (2) LTBI. The system shown in FIG. 19B may therefore be used to characterise *M. tuberculosis* complex infection present in an individual as ATB or LTBI. The system shown in FIG. 19A is representative of the structure of models m19 to m22 considered in the Examples, in which the three wells are:
Output
(1), (3) and (4) for m19;
(1), (2) and (3) for m20;
(1), (2) and (4) for m21; and
(2), (3) and (4) for m22.

The output of the trained machine algorithm model represents information about the disease status of the individual. Information about the disease status of the individual is described in detail above.

The output may be of a discrete nature. For example, the output value may be a classification that either the input data is associated with the presence of a particular disease or the input data is associated with the absence of the particular disease. The particular disease may, for example, be *M. tuberculosis* complex infection.

The output may be of a continuous nature. For example, the output value may represent or consist of the probability that the input data is associated with the presence of a particular disease. The output value may represent or consist of the probability that the input data is associated with the absence of the particular disease.

A continuous output may, for example, be numerical. A numerical cut-off may be applied in order to convert the continuous output to a discrete output. For example, an output value that (i) represents or consists of the probability that the input data is associated with the presence of a particular disease and (ii) is greater than a particular numerical cut-off may be converted to a classification that the input data is associated with the presence of the disease. An output value that (i) represents or consists of the probability that the input data is associated with the presence of a particular disease and (ii) is less than a particular numerical cut-off may be converted to a classification that the input data is associated with the absence of the disease. An output value that (i) represents or consists of the probability that the input data is associated with the absence of a particular disease and (ii) is greater than a particular numerical cut-off may be converted to a classification that the input data is associated with the absence of the disease. An output value that (i) represents or consists of the probability that the input data is associated with the absence of a particular disease and (ii) is less than a particular numerical cut-off may be converted to a classification that the input data is associated with the presence of the disease.

Method for Characterising a *M. tuberculosis* Complex Infection

The disclosure provides a method of using a trained machine learning algorithm model to characterise a *M. tuberculosis* complex infection present in an individual as active or latent, the method comprising: (a) receiving input data that comprises data derived from or consisting of image data of each of at least two wells of an enzyme-linked immunospot (ELISpot) assay for *M. tuberculosis* complex infection performed on a cell sample obtained from the individual; and (b) processing the input data using the trained machine learning algorithm model to generate an output representing information which characterises the *M. tuberculosis* complex infection as active or latent.

Active and latent *M. tuberculosis* complex infections are well-defined in the art. In brief, latent tuberculosis infection (LTBI) is a state of persistent immune response to stimulation by *M. tuberculosis* antigens without evidence of clinically manifested active tuberculosis. An individual having LTBI is infected with the *M. tuberculosis* bacteria but does not show symptoms of tuberculosis disease. In essence, the immune system keeps the bacterium in check, without eliminating it. An individual having LTBI may be incapable of transmitting *M. tuberculosis* bacteria.

Active tuberculosis infection (ATB) is associated with clinical signs of tuberculosis disease. General symptoms of tuberculosis may include loss of appetite, weight loss, fever and/or fatigue. Pulmonary tuberculosis may be associated with respiratory symptoms such as a persistent cough and/or breathlessness. Symptoms of extra-pulmonary tuberculosis may depend on the affected tissue or organ, and may include confusion, headache, seizures, abdominal pain and/or pain and loss of movement in an affected bone or joint. ATB may result from a new infection with *M. tuberculosis* bacteria. Alternatively, ATB may develop from LTBI.

Accordingly, a combination of clinical information and diagnostic testing may traditionally be used to determine the presence of ATB or LTBI in an individual. For example, the presence of ATB may be determined if the individual has (i) clinical signs of tuberculosis and (ii) *M. tuberculosis* bacteria. The presence of LTBI may be determined if the individual (a) does not have ATB but (b) has a *M. tuberculosis*-specific immune response. The presence of *M. tuberculosis* bacteria may, for example, be determined using culture or a nucleic acid amplification test such as, Gene Xpert MTB/RIF (Cepheid Inc.). The presence of A *M. tuberculosis*-specific immune response may, for example, be determined using an IGRA-based test, for example an ELISpot IGRA assay, such as a T-SPOT.TB test.

The method described herein for characterising a *M. tuberculosis* complex infection is advantageous compared to traditional methods for determining the presence of ATB or LTBI in an individual, because it does not require clinical information about the individual, or tests for the presence of *M. tuberculosis* bacteria. Rather, the presence of ATB or LTBI can be determined using only an ELISpot assay, such as a T-SPOT.TB test, which is already routinely employed to determine the presence or absence of *M. tuberculosis* complex infection. Furthermore, the method described herein may be performed using a blood sample obtained from the individual, whereas traditional methods based on Gene Xpert MTB/RIF or culture require a sputum sample. It is simple to obtain a blood sample for use in the method described herein. In contrast, a sputum sample is typically more difficult to obtain, especially in juvenile and elderly patients. The method described herein may thus be more easily performed than traditional methods for determining the presence of ATB or LTBI in an individual.

Input Data

Input data is described in detail above in connection with a method for obtaining information about the disease status of an individual. Any of the aspects described above may also apply to the method for characterising a *M. tuberculosis* complex infection.

Trained Machine Learning Algorithm Model

Trained machine learning algorithm models are described in detail above in connection with a method for obtaining information about the disease status of an individual. Any of the aspects described above may also apply to the method for characterising a *M. tuberculosis* complex infection.

Output

The output of the trained machine algorithm model represents information which characterises the *M. tuberculosis* complex infection as active or latent. ATB and LTBI are described in detail above.

The output may be of a discrete nature. For example, the output value may be a classification that either the input data is associated with ATB or the input data is associated with LTBI.

The output may be of a continuous nature. For example, the output value may represent or consist of the probability that the input data is associated with ATB. The output value may represent or consist of the probability that the input data is associated with LTBI.

A continuous output may, for example, be numerical. A numerical cut-off may be applied in order to convert the continuous output to a discrete output. For example, an output value that (i) represents or consists of the probability that the input data is associated with ATB and (ii) is greater than a particular numerical cut-off may be converted to a classification that the input data is associated with ATB. An output value that (i) represents or consists of the probability that the input data is associated with ATB and (ii) is less than a particular numerical cut-off may be converted to a classification that the input data is not associated with ATB, or is associated with LTBI. An output value that (i) represents or consists of the probability that the input data is associated with LTBI and (ii) is greater than a particular numerical cut-off may be converted to a classification that the input data is associated with LTBI. An output value that (i) represents or consists of the probability that the input data is associated with LTBI and (ii) is less than a particular numerical cut-off may be converted to a classification that the input data is not associated with LTBI, or is associated with ATB.

Method for Training a Machine Learning Algorithm Model

The disclosure also provides a method of training a machine learning algorithm model to generate information about the disease status of an individual, the method comprising training the machine learning algorithm model using a plurality of training data units, each training data unit comprising (i) input data that comprises data derived from or consisting of image data of each of at least two wells of an enzyme-linked immunospot (ELISpot) assay performed on a cell sample obtained from a respective training individual and (ii) data representing information about the disease status of the respective training individual.

The machine learning algorithm model may therefore be provided with training data (plurality of training data units) from many individuals for whom disease status information is known. An aim of the training process is to enable the machine learning algorithm model to generate an output that accurately predicts disease status information for an individual for whom disease status information of interest is not known. The training process may achieve this by iteratively adjusting parameters defining the machine learning algorithm model until the machine learning algorithm model is able to accurately predict disease status information for the training individuals. The training process may thus involve comparisons between outputs of the machine learning model for the training individuals and the corresponding known disease statuses of the training individuals. The adjustment of parameters of the machine learning algorithm model may, for example, be performed by minimizing a loss function, for example using a gradient descent process. In some embodiments, a cross-validation process is performed. For instance, the plurality of training data units may be divided into k subsets. The machine learning algorithm model may be trained on all but one (i.e. k−1) of the subsets, and then evaluated on the subset that was not used for training. The process may be repeated k times, with a different subset reserved for evaluation (excluded from training) each time.

Training Data Units

A plurality of training data units is used to train the machine learning algorithm model. Each training data unit comprises (i) input data that comprises data derived from or consisting of image data of each of at least two wells of an enzyme-linked immunospot (ELISpot) assay performed on a cell sample obtained from a respective training individual and (ii) data representing information about the disease status of the respective training individual.

Input data is described in detail above in connection with a method for obtaining information about the disease status of an individual. Information about the disease status of an individual is also described in detail above in connection with a method for obtaining information about the disease status of an individual. Any of the aspects described above may also apply to the method for training a machine learning algorithm model.

The plurality of training data units may comprise a plurality of subsets of training data units. Each training data unit within a subset may be generated by performing an image adjustment process on input data used for a different training data unit. That is, the plurality of training data units may comprise one or more training data units in which the input data comprises data that is generated by performing an image adjustment process on the input data comprised in a different training data unit comprised in the plurality of training data units. The image adjustment process may comprise one or more of: (a) changing a brightness of the image data; (b) changing a contrast of the image data; and (c) processing the input data to rotate an image corresponding to one of the at least two wells in the image data about an axis through the centre of the image of the. For example, the image adjustment process may comprise (a); (b); (c); (a) and (b); (a) and (c); (b) and (c); or (a), (b) and (c).

Brightness refers to the overall lightness or darkness of an image. Therefore, changing a brightness of the image data may comprise making the image data lighter or darker. For example, the brightness may be changed to about 50%, about 60%, about 70% about 80%, about 90%, about 100%, about 110%, about 120%, about 130%, about 140% or about 150% of original brightness. Preferably, the brightness is changed to between 80% and 120% original brightness, such as between 85% and 115%, between 90% and 110%, or between 95% and 105% original brightness. Changing the brightness of the image data may result in the outline of the image becoming less distinct. To address this issue, a "frame" corresponding to the colour of the original image outline may be overlaid on the image data following a change to its brightness.

Contrast refers to the difference in brightness between objects or regions within an image. Changing a contrast of the image data may, therefore, comprise increasing or decreasing the difference in brightness between regions of the image data. Changing the contrast of the image data may result in the outline of the image becoming less distinct. To address this issue, a "frame" corresponding to the colour of the original image outline may be overlaid on the image data following a change to its brightness.

In rotating an image corresponding to one of the at least two wells in the image data about an axis through the centre image of the well, the well is preferably circular. In this case, the image may be circular or square. Preferably, the image is square. When the image is square, pixels that are left outside of the boundary of the original image following rotation may be discarded. Empty space that is left within the boundary of the original image following rotation may be filled with pixels of a colour corresponding to the colour of the background of the image. The term "background of the image" refers to parts of the image that do not represent the spots formed by performing the ELISpot assay. The colour of the background of the image may, for example, be white.

Any degree of rotation may be applied. Preferably, the degree of rotation is from about 0° to about 359°, such as from about 45° to about 315°, about 90° to about 270°, about 135° to about 225°, or about 180°. The input data may comprise plural individual data units, each individual data unit being derived from or consisting of image data of a different respective one of the at least two wells. In this case, one or more of the individual data units may be processed to rotate an image corresponding to the well in the image data about an axis through the centre of the image of the well. The input data may comprise data derived from or consisting of image data representing a composite image containing images of all of the at least two wells. In this case, the input data may be processed to rotate one or more of the images comprised in the composite image about an axis through the centre of the image of the well. Rotation of one or more of the images comprised in the composite image, rather than the composite image itself, preserves the position of the images comprised in the composite image. This is important because the position of the images comprised in the composite image may correspond to the position of ELISpot wells each subjected to a different stimulus regimen.

The image adjustment process provides a technical advantage. In particular, the image adjustment process generates additional training data units, thereby increasing the size of the plurality of training data units used to train the machine learning algorithm model. The image adjustment process also generates diversity between training data units, for instance in terms of brightness and/or contrast. The inclusion of diverse training data units in the plurality of training data units used to train the machine learning algorithm model may improve the robustness of the model, by simulating differences in image data obtained by different image capture devices.

Machine Learning Algorithm Model

Machine learning algorithm models are described in detail above in connection with a method for obtaining information about the disease status of an individual. Any of the aspects described above may also apply to the method for training a machine learning algorithm model.

Outputs

Outputs are described in detail above in connection with a method for obtaining information about the disease status of an individual. Any of the aspects described above may also apply to the method for training a machine learning algorithm model.

Computer Program

Computer programs may be provided that comprise instructions that, when executed by a computer system, instruct the computer system to perform the method of any of the embodiments of the present disclosure.

The computer program may embody a method described herein as code (e.g. software code) and/or data. Such code and data can be stored on one or more computer-readable medium, which may include any device or medium that can store code and/or data for use by a computer system. When a computer system reads and executes the code and/or data stored on a computer-readable medium, the computer system performs the methods and processes embodied as data structures and code stored within the computer-readable storage medium. In certain embodiments, one or more of the steps of the methods and processes described herein can be performed by a processor (e.g., a processor of a computer system or data storage system). It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data.

Apparatus and System

Data processing apparatus may be provided that comprises a processor configured to perform the method of any of the embodiments of the present disclosure. To perform the method, the processor may execute the computer program mentioned above.

The data processing apparatus may further comprise an input device configured to receive the input data. The data processing apparatus may further comprise an output device configured to output the output generated by the machine learning algorithm model.

The disclosure also provides a system for obtaining information about the disease status of an individual, comprising: the data processing apparatus of an embodiment of the disclosure; and an image capturing device configured to capture the image data. The image capturing device may, for example, comprise an ELISpot plate reader. This would permit the system to both read the plate in which the ELISpot assay is performed, and analyse image data obtained from the plate.

EXAMPLES

Methods

Classifying Samples Providing T-SPOT TB Test Results

For models classifying positive test results as ATB or LTBI, two sources of T-SPOT.TB positive test result images were used: samples from internal studies, and clinical studies. For samples from internal studies no clinical information was available about the donors so a simulated tuberculosis status was generated based on the ratio of MaxTBAg: PHA spot count. The ratio of MaxTB Ag:PHA spot count was defined as the ratio of the human verified spot count of the antigen panel well with the largest response to the spot count for the positive control well. A cut-off of 0.3 was used to classify the samples as simulated-ATB (>0.3) or simulated-LTBI (<0.3). A total of 4615 T-SPOT.TB samples were included in this dataset; 652 samples were defined as simulated-ATB and 3963 samples were defined as simulated-LTBI. The samples were then split into a training set of 3660 samples (9510 simulated-ATB, 3150 simulated-LTBI) and a testing set of 955 (142 simulated-ATB and simulated-813 LTBI).

For samples from clinical studies (Barcelona and South Africa), tuberculosis status was classified based on the donor's clinical information. ATB patients were defined as confirmed tuberculosis positive (GeneXpert or culture-confirmed positive) and symptoms, while LTBI patients were defined as active tuberculosis disease excluded, T-SPOT.TB positive test. A total of 571 T-SPOT.TB samples were included in this dataset; 222 samples were defined as ATB and 349 samples were defined as LTBI. The samples were then split into a training set of 458 samples (178 ATB, 280 LTBI) and a testing set of 113 (44 ATB and 69 LTBI).

For models classifying T-SPOT.TB test result as positive or negative, test result images were sourced from internal studies. Each sample had a positive or negative result assigned by an experienced operator according to the T-SPOT.TB package insert (by applying the 6 spot cut-off). Under US-specific Package Insert guidance, the test is interpreted as positive if the spot count in either antigen panel well minus the spot count in the nil control well (normalised spot count) it greater than or equal to 8 spots. A normalised antigen spot count response of less than 5 spots is interpreted as a negative result. Responses between 5 and 7 spots inclusive are considered borderline. For this training set, borderline negative samples (5 spots) were considered negative and borderline positive samples (6 and 7 spots) were considered positive. 3729 valid T-SPOT.TB test result samples were included in this dataset. 617 samples had a positive T-SPOT.TB result while the remaining 3112/3729 were negative. The dataset of T-SPOT.TB composite images were randomly split 80%:20% to create a training and a testing dataset.

Image Acquisition

All T-SPOT.TB test plates were scanned on an Immunospot S6 core analyser (Cellular Technology Limited, Ohio, USA). Four individual 518×518 resolution image files were generated for each T-SPOT.TB test sample: an image of the nil well membrane, panel A well membrane, panel B well membrane, and the positive control (PHA) well membrane. Individual image files were used to train and test single-well image convolutional neural networks (CNN) models.

For four-well composite image machine learning applications, a 518×2036 resolution composite image was created for each sample containing all four well membrane images (FIG. 1). Composite images were assigned a unique identification number which mapped to the anonymised clinical status. Composite four-well image files were used to train and test four-well image convolutional neural networks (CNN) models.

Image Augmentation

Figure 2:
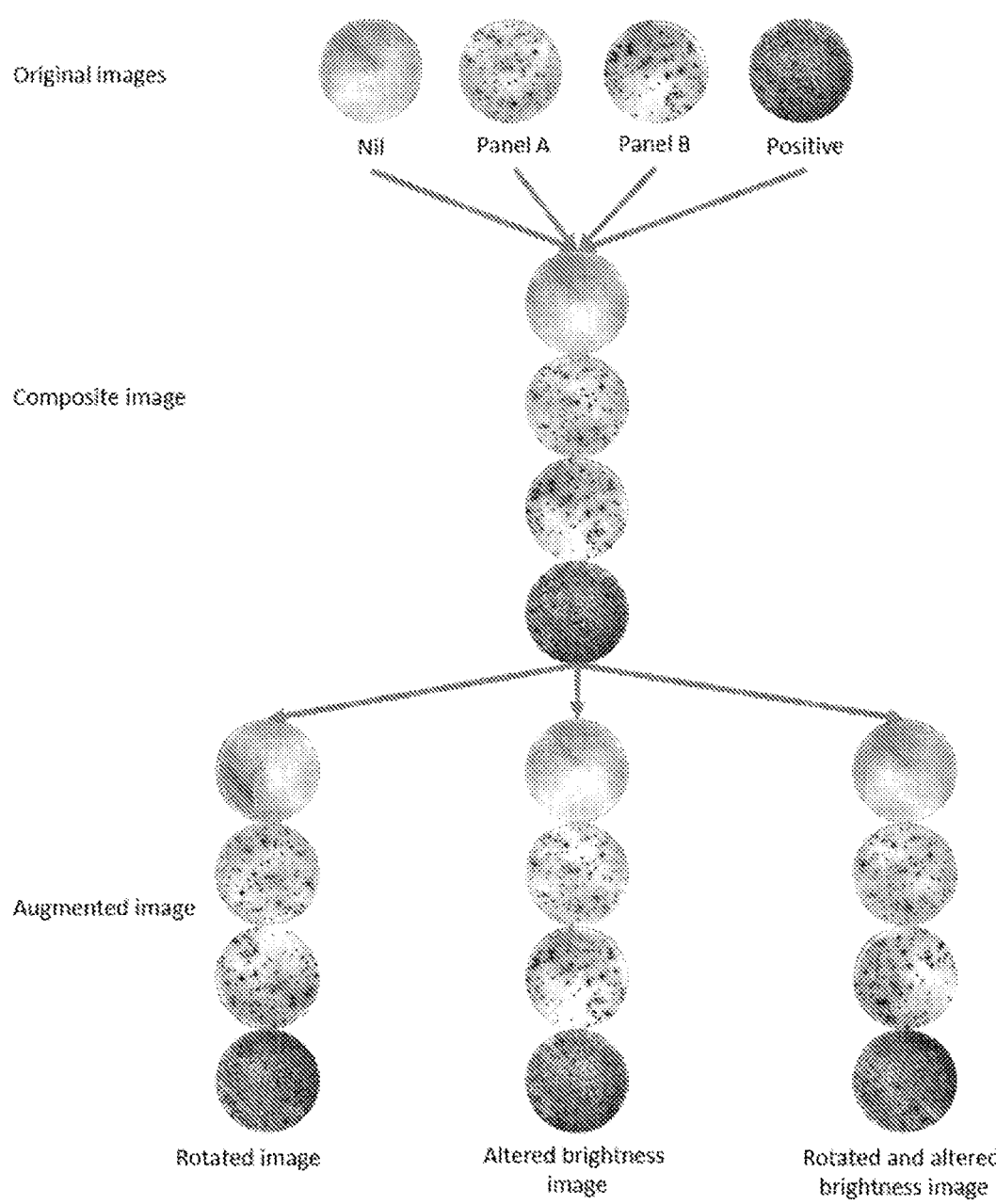
FIG. 2: Composite image and image augmentation. Individual well images were combined to create a single four-well composite image for each sample. Rotation and brightness image augmentation was applied to composite images from the training datasets only.
Figure 3:
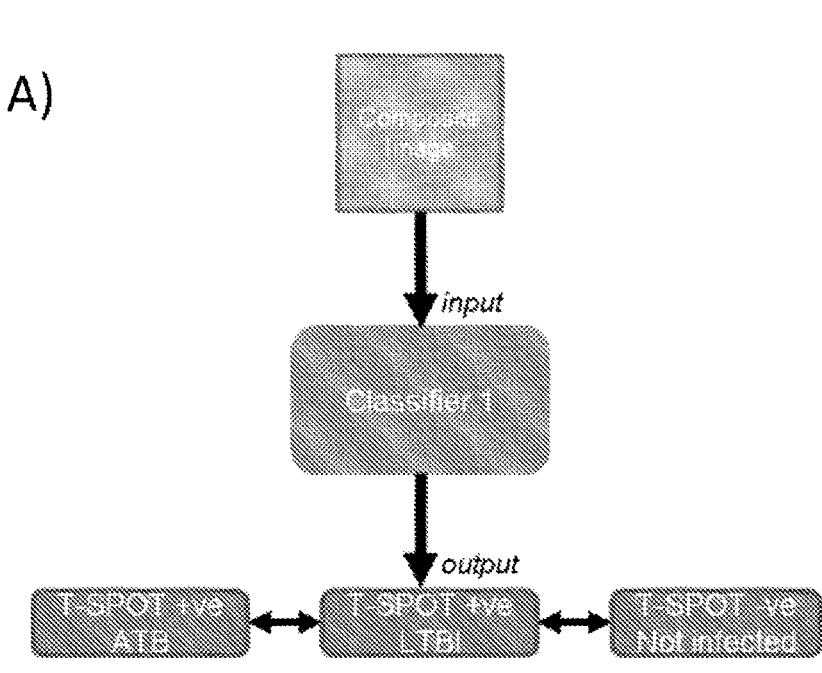
FIGS. 3 to 9: Systems diagrams showing the steps comprised in exemplary trained machine learning algorithm models.
Figure 3:
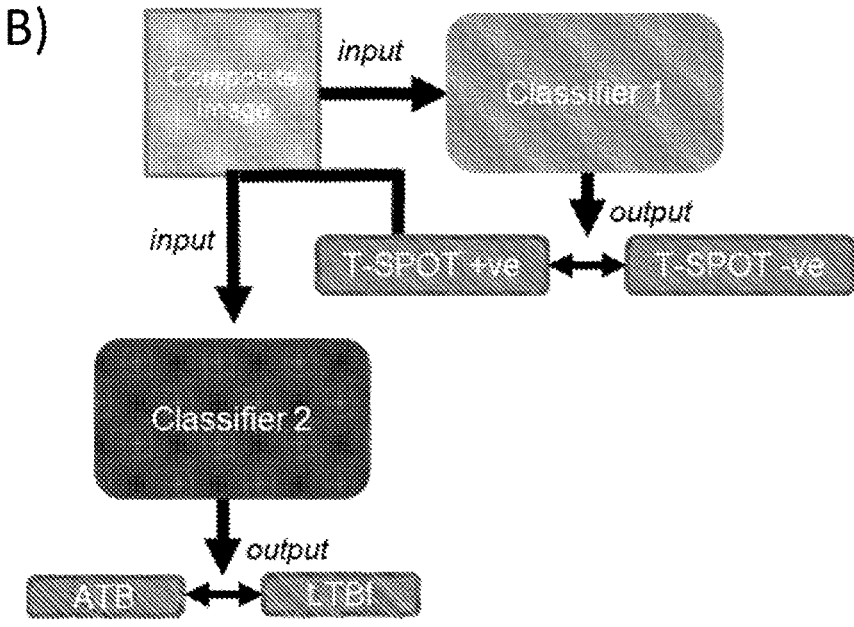
Figure 4:
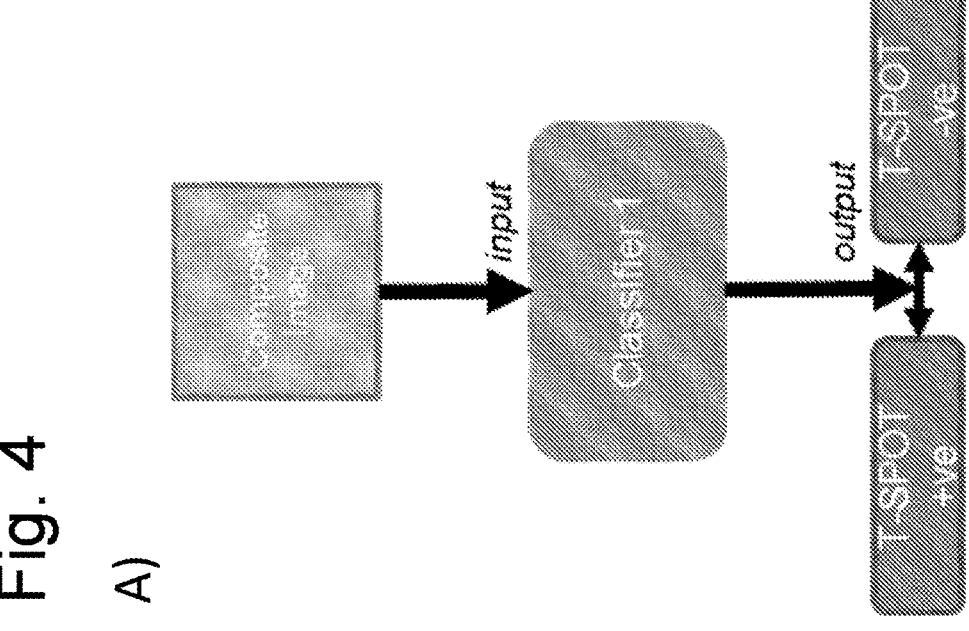
Figure 4:
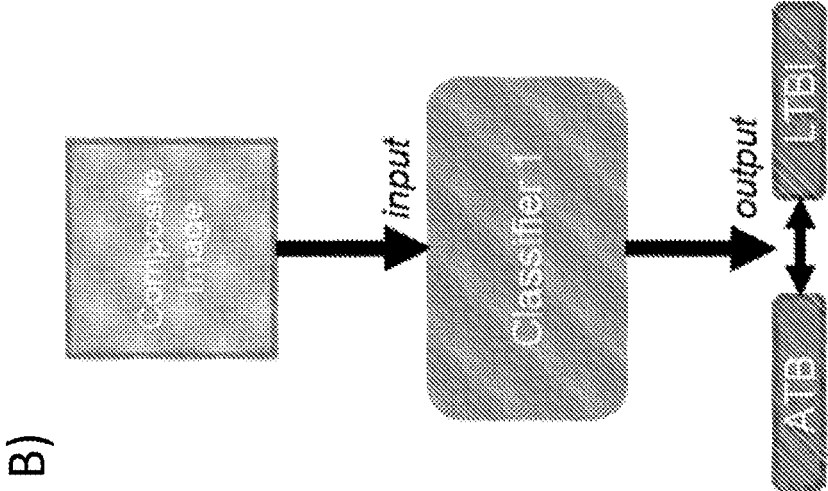

Image augmentation strategies were applied to the single well images and four-well composite images (composite images) in the training data sets in order to increase the effective dataset size. As the position of the wells in the composite image are required for the correct interpretation of the test, full image rotation could not be used. However the orientation of individual wells within the composite image can be altered without altering the interpretation of the test. Therefore, the individual well membrane images were rotated by 90°, 180° and 270° then recombined into new composite images (FIG. 2).

The training dataset images were also augmented by altering the brightness of the original images. The brightness of original and rotated images were altered by random values between 80% and 120% original brightness. A white frame image was overlaid on the brightness-modified composite image to preserve the original frame colour (FIG. 2). No image augmentation was applied to samples in the testing dataset. For different models the training dataset were augmented with either one or both of the strategies as detailed above. Optimal level of dataset augmentation was determined empirically.

Machine Learning: Model Training and Assessment

Convolution neural network (CNN) is a version of machine learning and artificial intelligence which can pro- cesses, analyse and categorise complex images. CNNs are commonly used in many consumer technology fields such as social media and AI assistants. The computer software is trained on a set of known images and learns how to differentiate between the categories. The trained algorithm is then used to categorise unseen images.

CNN models were created using open-source machine learning libraries TensorFlow and Keras. CNN models were trained on the single well images or composite images from the appropriate training dataset. Training was monitored using classifier accuracy and binary cross entropy as the loss function.

Fully-trained model performance was assessed using reserved testing datasets. 80% of the total clinical sample test images were used for the training set, whilst 20% (randomly selected) were reserved and used only as the testing set. The same testing set was applied to all CNN model algorithms and no image augmentation was applied to the testing set.

The CNN models produce a binary classification prob- ability, for ATB or LTBI. These values (predicted score/ discrimination index) were used to determine ROC curve, ROC-AUC, and sensitivity and specificity of the classifiers using GraphPad Prism (GraphPad Software).

Results

Example 1

Example 1 shows that CNN models trained on single well T-SPOT.TB test images differentiate tuberculosis status bet- ter than individual well spot count data.

The T-SPOT.TB test consists of four wells where PBMCs are incubated with media (nil control), 2 wells of tubercu- losis antigens (panel A and panel B wells) and a mitogen control well (positive control). The antigen panel with the largest spot count response is defined as the maximum antigen. Five different CNN models were trained on nil well images (m1), panel A well images (m2), panel B well images (m3), positive control well images (m4) and maximum antigen well images (m5).

Figure 10:
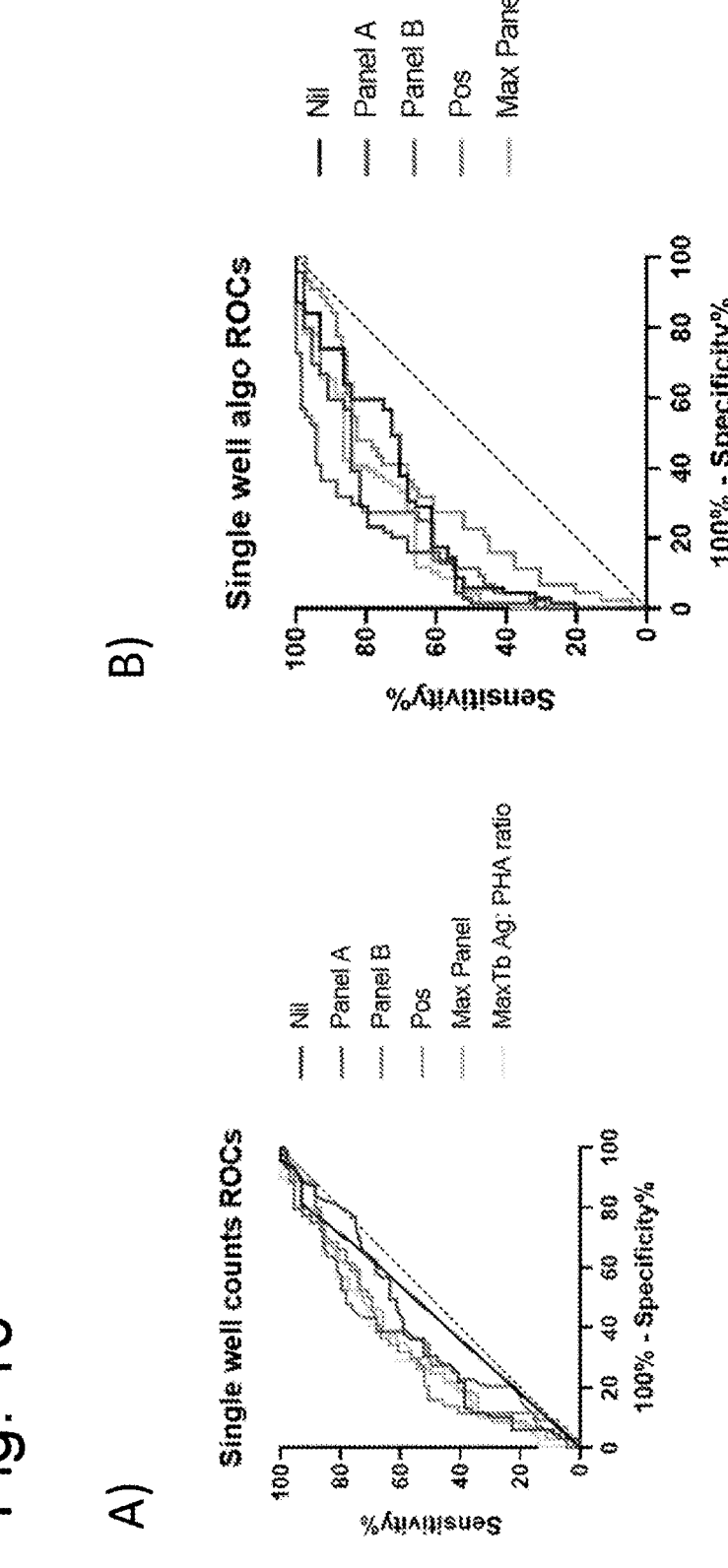
FIG. 10: CNN models (m1-m5) trained on single well images and their ability to distinguish tuberculosis status. A) ROC curves showing performance of spot count data. B) ROC curves showing performance of single well model algorithms (trained on m1-nil, m2-Panel A, m3-Panel B, m4-positive (PHA), m5 maximum antigen panel spot count). Dotted line indicates an AUC of 0.5

To compare the ability of the single-well models (m1-m5) to differentiate tuberculosis status versus the ability of individual well spot count data and MaxTb Ag: PHA spot count ratio to differentiate ATB versus LTBI, spot counts were enumerated in all wells for T-SPOT.TB test result images from 113 donors with defined tuberculosis status. For the same sample, the test result images were processed by the five single well algorithm models (m1 to m5). Results from spot count data and single well model algorithms were analysed by ROC curve (FIG. 10). Nil, panel A, panel B and positive control well spot count data were poor predictors of tuberculosis status with ROC-AUCs of 0.550, 0.603, 0.645 and 0.658 respectively. The maximum antigen spot count data and MaxTb Ag: PHA spot count ratio had similar performance to the individual well spot count data with ROC-AUC of 0.651 and 0.677 respectively.

All single well model algorithms (m1-m5) differentiated tuberculosis disease status better than individual well spot count data with ROC-AUCs of 0.744 for nil well images (m1), 0.823 for panel A (ESAT-6) images (m2), 0.842 for panel B (CFP10) images (m3), 0.696 for PHA images (m4)

and 0.810 for maximum antigen images (m5). However, none of these models reached the minimum required per- formance at ROC-AUC of >0.85.

Example 2

Example 2 shows that CNN model (m6) trained on simulated MaxTb Ag: PHA spot count data set cannot be used to classify clinical T-SPOT.TB+'ve test result images.

Figure 11:
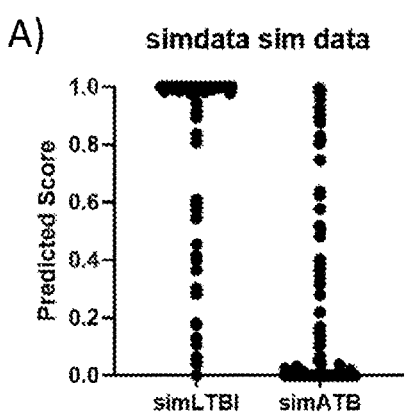
FIG. 11: CNN model (m6) trained on T-SPOT.TB+'ve result images with simulated TB status (using ratio of MaxTB Ag:PHA spot count). A) predicted score and ROC curve for test images with simulated TB status. B) predicted score and ROC curve for test images with confirmed TB status.
Figure 11:
Figure 11:
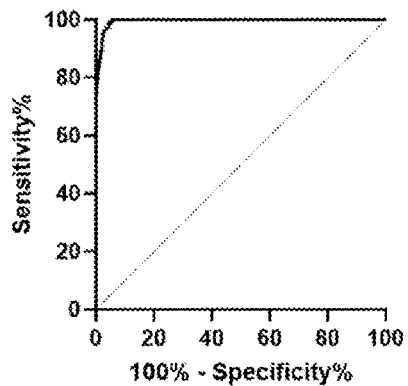
Figure 11:
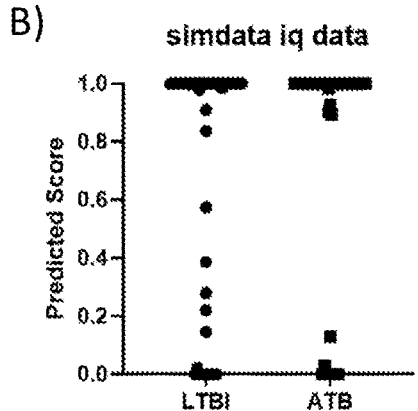
Figure 11:
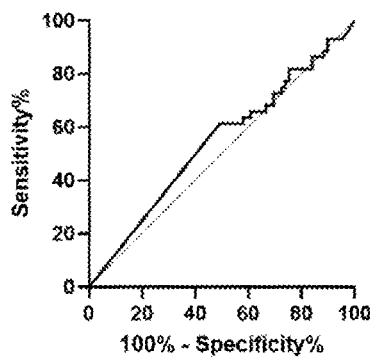

To assess the ability of ratio of MaxTb Ag:PHA spot count to be used to train CNN models a convolutional neural network was trained on T-SPOT.TB test composite images with assigned simulated TB status calculated from the MaxTb Ag: PHA spot count ratio (cut off at 0.3). The model (m6) achieved accuracy of 0.966 and a ROC-AUC of 0.995 when used to classify test composite images with an assigned simulated TB status (FIG. 11). However the model (m6) was then used to try to predict the TB disease status of clinical sample composite images. The model (m6) achieved an AUC-ROC of 0.541 and accuracy of 0.637, and was not able to differentiate TB status.

Figure 12:
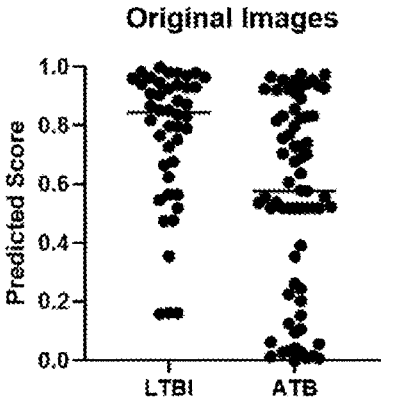
FIG. 12: Predicted Score of clinical sample T-SPOT.TB positive test results analysed by CNN models (m7-m10).
Figure 12:
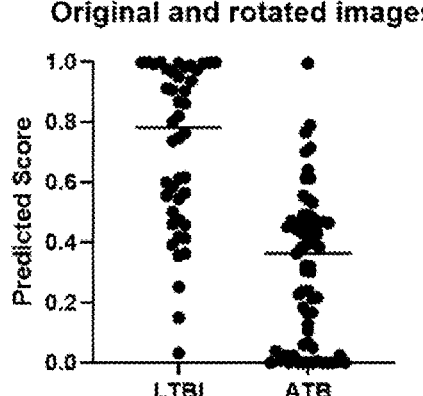
Figure 12:
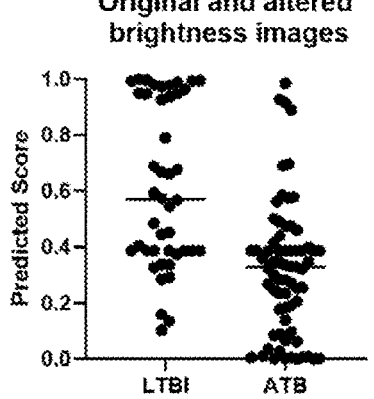
Figure 12:
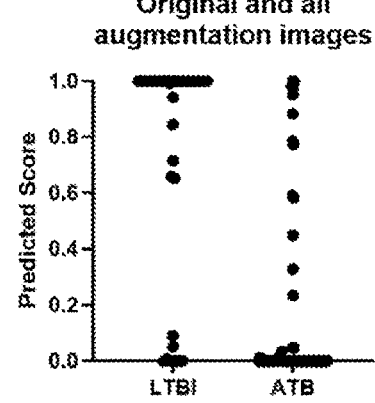
Figure 13:
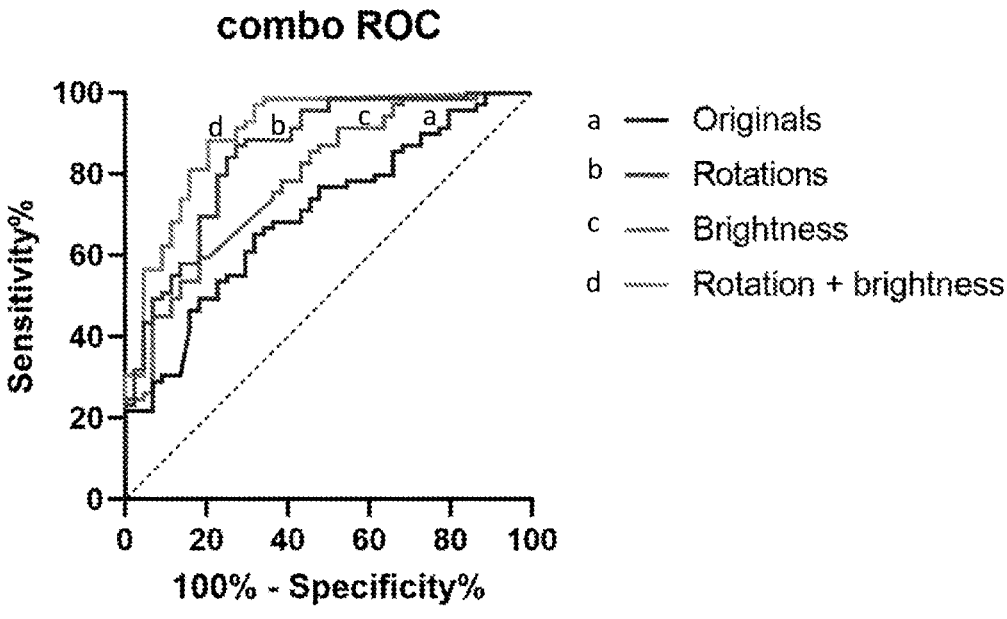
FIG. 13: Receiver Operator Curve showing performance for four composite image based CNN model classifiers (m7-m10) trained on clinical T-SPOT.TB+'ve test original and augmented images.

For Examples 3 to 5, CNN model output (m7-m10), by predicted score (differentiation index) is provided in FIGS. 12A-12D. FIG. 13 shows the ROC-AUC for each CNN model (m7-m10), whilst Table 1 provides the sensitivity and specificity data. CNN model (m7) trained on images clas- sified by clinical TB-status can classify T-SPOT.TB positive test result images by tuberculosis status.

Example 3

A CNN model (m7) was trained on T-SPOT.TB positive test result four-well composite images with clinically defined TB status. The training set for this model consisted of only original four-well composite images (with no image augmentation). When the test dataset was analysed using this model (m7, FIG. 12A, FIG. 13, Table 1) the ROC-AUC was 0.700 with sensitivity of 71.0% and specificity of 56.8% at a cut-off of 0.8172.

TABLE 1

ROC-AUC and sensitivity and specificity for CNN models m7-m10. four-well composite image model performance

| Model | Training data | ROC-AUC | Sensitivity | Specificity | Cut-off |
|---|---|---|---|---|---|
| m7 | Original images only | 0.700 | 71.0% | 56.8% | 0.8172 |
| m8 | Original + rotated images | 0.854 | 88.4% | 70.45% | 0.5549 |
| m9 | Original + altered brightness images | 0.786 | 86.9% | 52.3% | 0.5651 |
| m10 | Original + rotated and altered brightness images | 0.900 | 91.3% | 72.7% | 0.8153 |

As only a limited number of T-SPOT.TB positive test result data was available with a defined clinical status, dataset augmentation was used to increase the effective size of the training dataset. To ensure that the new composite images remained valid, individual well images for the T-SPOT.TB test result were rotated while the order of wells in the composite image remained constant. The training set of the model (m8) consisted of original composite images plus rotated composite images. The proportion of additional augmented images in the dataset was determined empiri- cally. This model (m8) showed improved performance com- pared to the initial model (m7) (FIG. 12B, FIG. 13, Table 1)

with a ROC-AUC of 0.854 with sensitivity of 88.4% and specificity of 70.45% at a cut-off of 0.5549.

Example 4

An improvement for the augmentation dataset approach was also investigated. It was observed that samples incorrectly categorised by the initial model tended to have high levels of non-specific staining, such that the composite images were darker in appearance. To address this issue the training dataset used augmented composite images wherein the brightness was modified by a random value between 80% and 120%. The proportion of additional augmented images in the dataset was determined empirically. This model (m9) also showed a performance increase compared to the initial (m7) model (FIG. 12C, FIG. 13, Table 1) with a ROC-AUC of 0.786 with sensitivity of 86.9% and specificity of 52.3% at a cut-off of 0.5651.

Example 5

Following the increase in performance from the two augmentation strategies, these were then combined for the final CNN model. Augmented rotated well composite images were created, then the rotated and original composite image dataset was further augmented by modifying the image brightness (as described in Examples 3 and 4).

The use of both image augmentation techniques improved the performance of the model algorithm for differentiating TB status. The model (m10) trained on images augmented with rotation and brightness performed the best and was able to differentiate ATB v LTBI with a ROC-AUC of 0.900 and sensitivity of 91% and specificity of 72% at a cut off of 0.8156 (see FIG. 12D, FIG. 13 and Table 1).

Example 6

CNN model (m11) trained on T-SPOT.TB result image dataset can be used to classify T-SPOT.TB test result images as either positive or negative test result for MTB infection.

T-SPOT.TB results are interpreted by enumerating tuberculosis specific spots.

Figure 14:
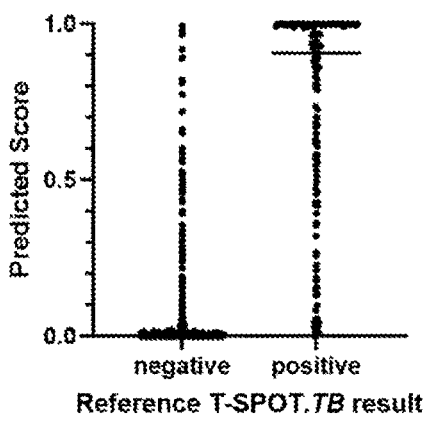
FIG. 14: Predicted score and ROC curve of CNN model (m11) trained on T-SPOT.TB positive and negative result composite images.
Figure 14:
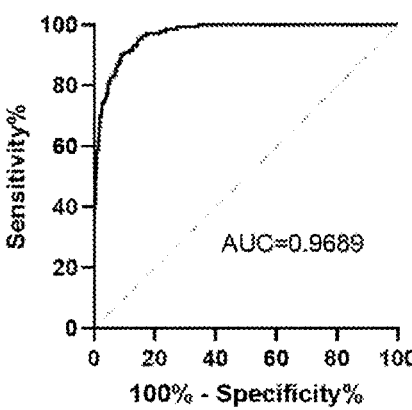

To assess the ability of CNN to interpret T-SPOT.TB test result images a CNN model was trained on positive and negative T-SPOT.TB test result images. Composite well images were created from 3729 valid T-SPOT.TB test samples. Each sample had a positive or negative result assigned by an experienced operator as previously described above. 16.5% (617/3729) of the dataset had a positive T-SPOT.TB result while the remaining 83.5% (3112/3729) were negative. The dataset of T-SPOT.TB result composite images were randomly split 80%:20% to create a training and a testing dataset. Data augmentation (well rotation and image brightness) was applied to the training set as described previously. A CNN model (m11) was trained on the augmented training dataset and model performance was assessed with the non-augmented test dataset (FIG. 14). The model was able to differentiate positive and negative T-SPOT.TB results with a ROC-AUC of 0.9689. At the optimal cut-off of 0.1263, the model could classify T-SPOT.TB test positive and test negative samples with 90.8% sensitivity, 90.2% specificity and 90.7% accuracy. It is contemplated that the outlined method for discriminating ELISPOT positive results vs negative results could be implemented, where the input data is provided for example, as an TB-IGRA ELISPOT result images, such as T-SPOT.TB test result images and then application of the machine learning algorithm automatically outputs a test result report. Additionally, a machine learning algorithm, as contemplated by e.g. CNN model m11, may be integrated or combined sequentially with a model which discriminates ATB from LTBI (such as e.g. CNN model m10) such that any positive test result samples are then automatically analysed and classified based on characteristic of disease status, i.e. ATB or LTBI.

Example 7

The T-SPOT.COVID test is a standardised ELISPOT (Enzyme Linked ImmunoSpot) based technique intended for qualitative detection of a cell mediated (T cell) immune response to SARS-CoV-2 in human whole blood. The T-SPOT.COVID test is intended for use as an aid in identifying individuals with an adaptive immune response to SARS-CoV-2, specifically the T cell response.

Figure 15:
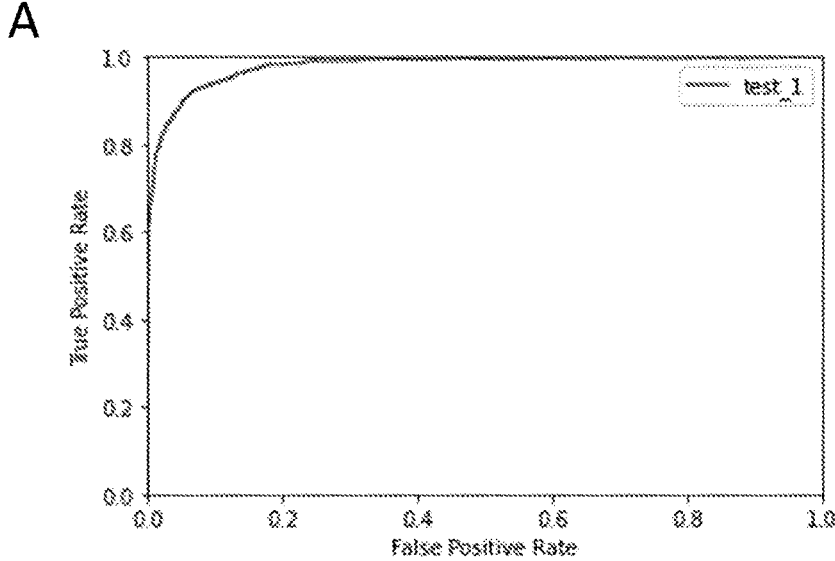
FIG. 15: Tuberculosis result classifier M11 can determine COVID-reactivity. 3141 composite images of T-SPOT.COVID samples were analysed using model m11. A) Receiver operator curve, B) Confusion matrix. Predicted labels were determined using a default 0.5 cut-off.
Figure 15:
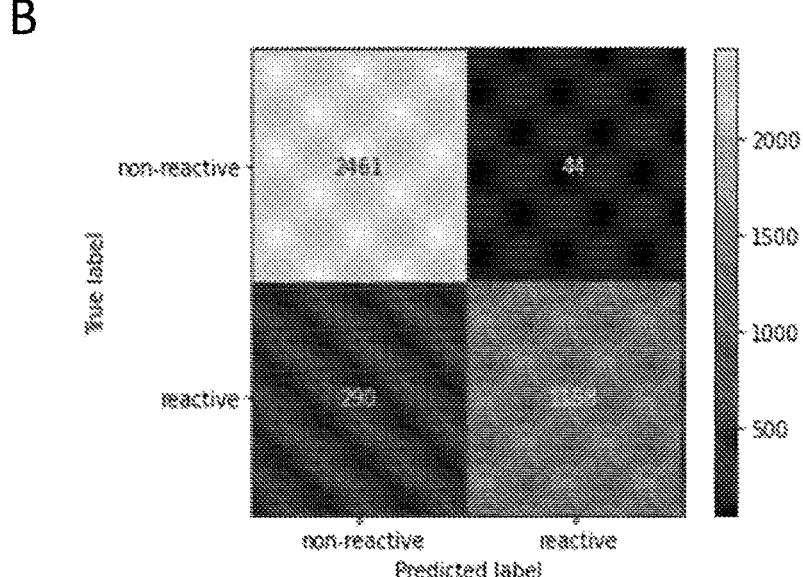

Model m11 was trained on T-SPOT.TB test result images and categorises sample as TB-positive or TB-negative (see Example 6). To determine if this model can determine the status of other disease states, model m11 was used to analyse T-SPOT.COVID test result images (FIG. 15). The predicted score had an area under the ROC curve of 0.980. Compared to results generated by a trained human operator following the T-SPOT.COVID instructions for use, the model had accuracy of 91.6%, positive agreement of 80% and negative agreement of 98.2% at a cut-off of 0.5.

Example 8

3,141 T-SPOT.COVID test result images were used to train a classifier model to predict SARS-CoV2 T-cell reactive status donors (model m12; see FIG. 16). 812 T-SPOT.COVID test result images were reserved and used to assess the classifier's performance. All T-SPOT.COVID samples consisted of four wells (nil, COV panel A, COV panel B, positive control) and the test result were classified as reactive or non-reactive based on a 6-spot cut-off by an experienced operator following T-SPOT.COVID instructions for use.

Figure 17:
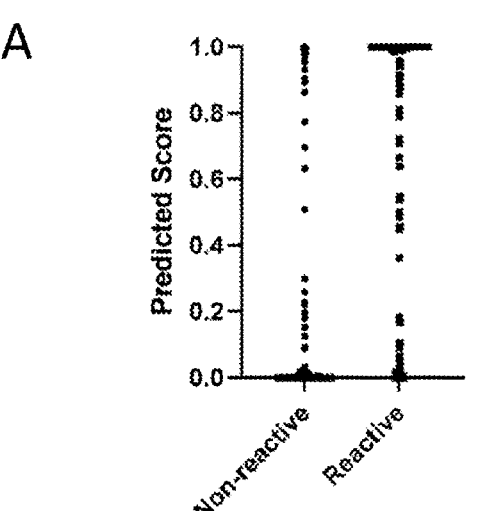
FIG. 17: T cell-reactivity to SARS-CoV2. A) Output score from COVID-trained classifier, b) ROC curve of output scores. C) agreement between true labels and predicted labels using a cut-off of 0.5.
Figure 17:
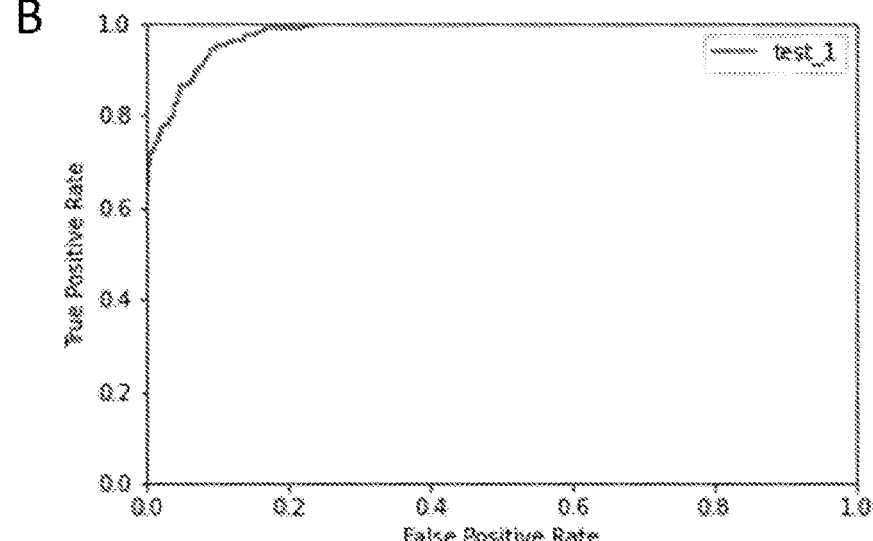
Figure 17:
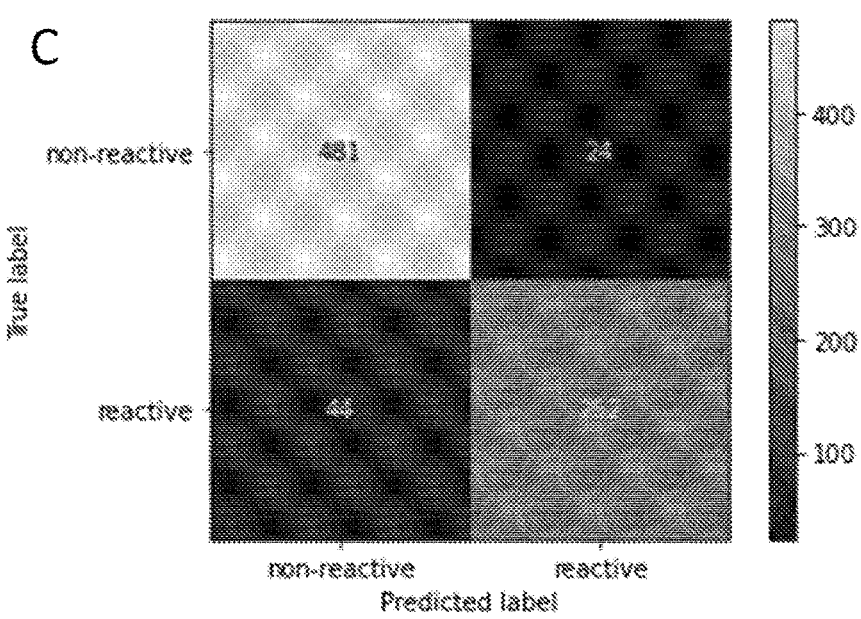

Model m12 was trained on four well composite images labelled with the operator-determined result. To assess the performance of the trained model a reserved test set of 812 composite images were used. The ROC-AUC was 0.980 with 91.5% accuracy, 91.3% sensitivity and 91.6% specificity using a cut-off of 0.5 (FIG. 17).

Example 9

Figure 18:
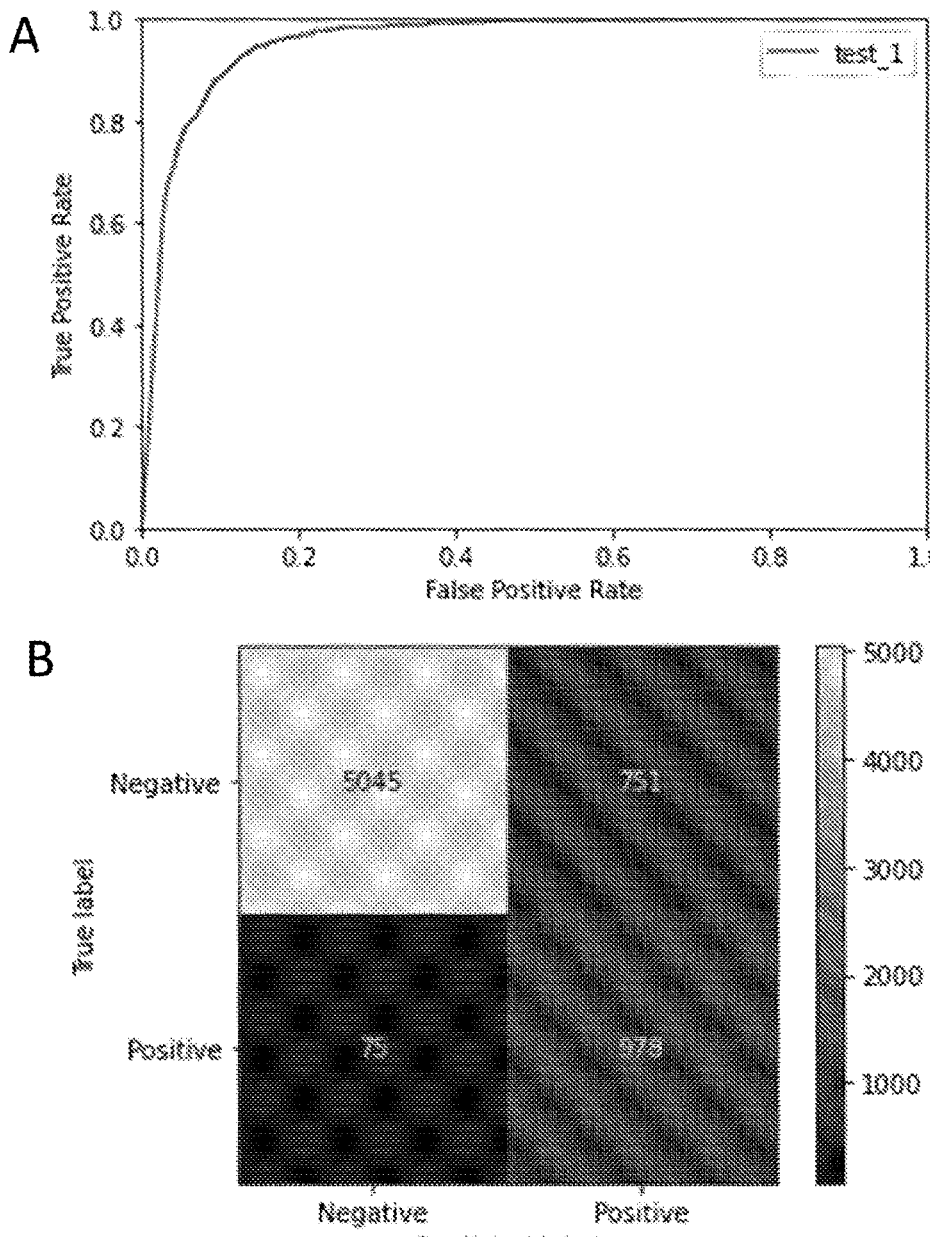
FIG. 18: COVID result classifier Model m12 can determine tuberculosis results. 6849 composite images of T-SPOT.COVID samples were analysed using model m12X. A) receiver operator curve B) Predicted labels were determined using a default 0.5 cut-off.
Figure 19:
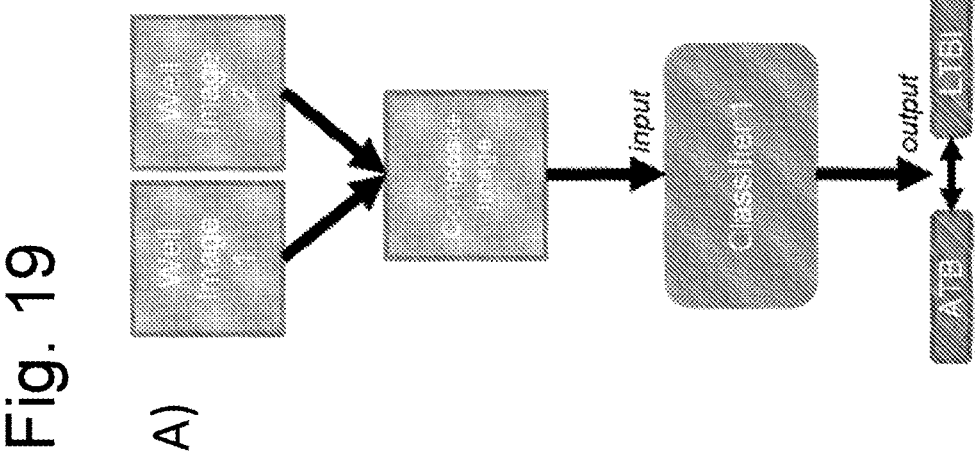
FIG. 19: System diagram showing the steps comprised in exemplary trained machine learning algorithm models using two and three well composite images, reflective of classifier models m13 to m22. A) m13 to m18 use images of two wells to form the composite image used as input to the classifier. B) m19 to m22 use images of two wells to form the composite image used as input to the classifier.
Figure 19:
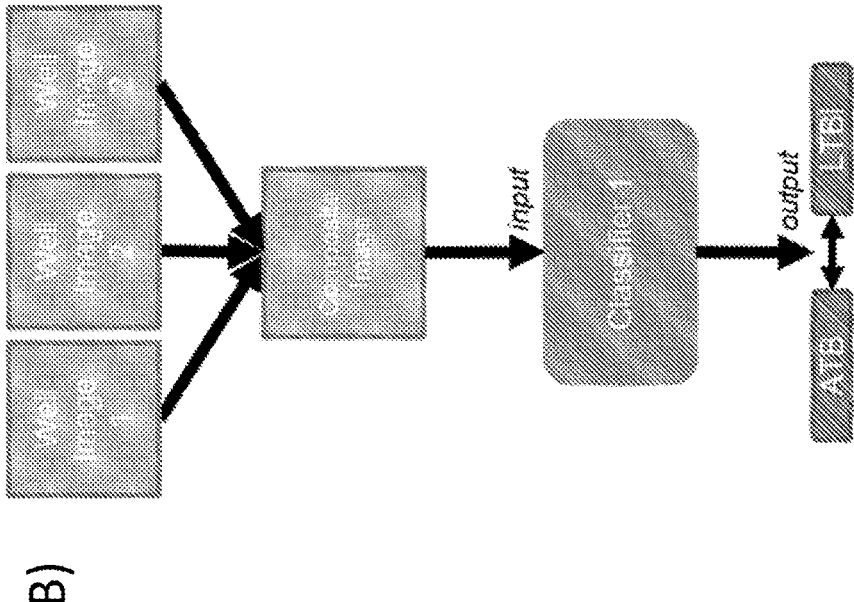

To determine model m12 can determine the status of disease states other than COVID-status, model m12 was used to analyse T-SPOT.TB test result images (FIG. 18). The predicted score had an area under the ROC curve of 0.956. Compared to results generated by a trained human operator following the T-SPOT.COVID instructions for use, the model had accuracy of 88.5%, positive agreement of 56.6% and negative agreement of 98.5% at a cut-off of 0.5.

Example 10

To determine if two or three well composite images could be used to train a model to differentiate samples based on TB disease status models m13 to m22 were trained using the specific combination of well images described in table 2. Models trained on 2 wells (m13 to m18) produced accuracy ranging from 68 to 84% when assessed on a reserved test set (table 2). The two-well model with the highest accuracy and ROC-AUC was trained on the two antigen wells, panel A and panel B. Three-well models (m19 to m22) produced accuracy ranging from 76 to 79% when assessed on a reserved test set. The three well model with the highest accuracy and ROC-AUC was trained on the two antigen wells and the positive control.

TABLE 2 two-well and three-well composite image
trained tuberculosis disease status classifiers.

| Model | Number of images | Wells | Accuracy (%) | ROC-AUC (%) |
|---|---|---|---|---|
| m13 | 2 | Nil, PA | 74.34 | 0.823 |
| m14 | 2 | Nil, PB | 70.80 | 0.793 |
| m15 | 2 | Nil, PHA | 71.68 | 0.801 |
| m16 | 2 | PA, PB | 84.07 | 0.842 |
| m17 | 2 | PA, PHA | 77.88 | 0.863 |
| m18 | 2 | PB, PHA | 67.26 | 0.745 |
| m19 | 3 | Nil, PA, PB | 76.11 | 0.871 |
| m20 | 3 | Nil, PA, PHA | 77.88 | 0.837 |
| m21 | 3 | Nil, PB, PHA | 78.76 | 0.790 |
| m22 | 3 | PA, PB, PHA | 79.65 | 0.833 |

The invention claimed is:

1. A method to characterise a *Mycobacterium tuberculosis* (*M. tuberculosis*) complex infection present in an individual as active or latent, using a trained machine learning algorithm model stored on one or more computer-readable medium, the method comprising:

(a) receiving from an image capture device image data of each of at least two wells of an enzyme-linked immunospot (ELISpot) assay for *M. tuberculosis* complex infection performed on a cell sample obtained from the individual;

(b) generating input data by formatting the image data for conformity to be input to the trained machine learning algorithm model; and (c) processing the input data using the trained machine learning algorithm model to generate an output representing information which characterises the *M. tuberculosis* complex infection as active or latent.

2. The method of claim 1, wherein formatting the image data comprises at least one of:

(a) changing a brightness of the image data;

(b) changing a contrast of the image data; and (c) processing the input data to rotate an image corresponding to one of the at least two wells in the image data about a central axis through the image of the well.

3. The method of claim 1, wherein:

(a) the image data represents a composite image containing images of all of the at least two wells; and/or (b) the input data comprises plural individual data units, each individual data unit being derived from or comprising image data comprising a different respective one of the at least two wells.

4. The method of claim 1, wherein the input data further comprises data that is neither derived from nor comprises image data of a well of the ELISpot assay.

5. The method of claim 4, wherein the data that is neither derived from nor comprises image data of a well of the ELISpot assay comprises data obtained from the cell sample prior to or during performance of the ELISpot assay, optionally wherein the data obtained from the cell sample is derived from or comprises the number of cells comprised in the cell sample.

6. The method of claim 1, wherein a different stimulus regime is applied to the cell sample in each of the at least two wells.

7. The method of claim 6, wherein each stimulus regime is selected from:

(a) no stimulus;

(b) a known activator of cells comprised in the sample; and (c) an antigen, optionally wherein the sample comprises T cells and the known activator is a T cell activator, optionally phytohaemagglutinin (PHA).

8. The method of claim 7, wherein the antigen is a *M. tuberculosis* antigen, optionally wherein the *M. tuberculosis* antigen comprises an ESAT-6 peptide or a CPF10 peptide.

9. The method of claim 1, wherein:

(a) the ELISpot assay is an interferon gamma release assay (IGRA), optionally wherein (i) the IGRA is a T-SPOT.TB assay or (ii) the information about the disease status of the individual comprises information relating to the presence or absence of a SARS-COV-2 infection in the individual and the IGRA is a T-SPOT.COVID assay; and/or (b) the machine learning algorithm comprises a neural network, optionally wherein the neural network comprises a convolutional neural network.

10. A non-transitory computer-readable storage medium storing a computer program comprising instructions that, when executed by a computer system, instruct the computer system to perform the method of claim 1.

11. A data processing apparatus comprising a processor configured to perform the method of claim 1.

* * * * *